US011091751B2

(12) United States Patent
Pelzer et al.

(10) Patent No.: US 11,091,751 B2
(45) Date of Patent: Aug. 17, 2021

(54) OPTIMIZATION OF THE EXPRESSION OF SERINE PROTEASES IN HOST CELLS

(71) Applicant: BRAIN Biotech AG, Zwingenberg (DE)

(72) Inventors: Alexander Pelzer, Bickenbach (DE); Bela Kelety, Frankfurt (DE)

(73) Assignee: BRAIN Biotech AG, Zwingenberg (DE)

( * ) Notice: Subject to any disclaimer, the term of this patent is extended or adjusted under 35 U.S.C. 154(b) by 0 days.

(21) Appl. No.: 16/616,401

(22) PCT Filed: May 30, 2018

(86) PCT No.: PCT/EP2018/064216
§ 371 (c)(1),
(2) Date: Nov. 22, 2019

(87) PCT Pub. No.: WO2018/220032
PCT Pub. Date: Dec. 6, 2018

(65) Prior Publication Data
US 2020/0140841 A1   May 7, 2020

(30) Foreign Application Priority Data

May 31, 2017   (EP) .................................... 17173813

(51) Int. Cl.
*C12N 9/64*   (2006.01)
*C12N 15/81*   (2006.01)
*C12P 21/02*   (2006.01)
*C07K 14/81*   (2006.01)

(52) U.S. Cl.
CPC ........ *C12N 9/6408* (2013.01); *C07K 14/8117* (2013.01); *C12N 15/815* (2013.01); *C12P 21/02* (2013.01)

(58) Field of Classification Search
CPC ............ C12N 9/64; C12P 21/06; C07H 21/04
See application file for complete search history.

(56) References Cited

U.S. PATENT DOCUMENTS

| 5,648,254 A | 7/1997 | Mulvihill et al. |
| 8,623,810 B2 | 1/2014 | Niehaus et al. |
| 2006/0269538 A1* | 11/2006 | Koltermann ............. C12N 9/64 424/94.63 |

FOREIGN PATENT DOCUMENTS

| WO | WO 94/00483 A1 | 1/1994 |
| WO | WO 98/12211 A1 | 3/1998 |
| WO | WO 00/01831 A2 | 1/2000 |
| WO | WO 2010/099955 A1 | 9/2010 |
| WO | WO 2018/220032 A1 | 12/2018 |

OTHER PUBLICATIONS

"Extended European Search Report dated Sep. 18, 2017 in Europe Patent Application No. 17173813.1, filed on May 31, 2017", 18 pages.
"International Search Report and Written Opinion dated Oct. 5, 2018 in International Patent Application No. PCT/EP2018/064216, filed on May 30, 2018", 26 pages.
Anstead, et al., "Lucilia Cuprina Genome Unlocks Parasitic Fly Biology to Underpin Future Interventions", Nature Communications, 2015, 6(7344):12 pages.
Bebbington, C. R., et al., "High-level Expression of a Recombinant Antibody From Myeloma Cells Using a Glutamine Synthetase Gene as an Amplifiable Selectable Marker", Bio/Technology (Nature Publishing Company), Feb. 1992, 10(2):169-175.
Database Uniprot, "SubNanne: Full=Uncharacterized protein {ECO:0000313|EMBL:KNC33625.1}", retrieved from EBI accession No. UNIPROT: A0A0L0CMU2 Database accession No. A0A0L0CMU2, XP002773334, Nov. 11, 2015, 2 pages.
Degn, et al., "Recombinant Expression of the Autocatalytic Complement Protease MASP-1 is Crucially Dependent on Co-Expression with its Inhibitor, C1 Inhibitor", Protein Expression and Purification, 2013, 88(2):173-182.
Potvin, et al., "Bioprocess Engineering Aspects of Heterologous Protein Production in Pichia Pastoris: A Review", Biochemical Engineering Journal, May 15, 2012, 64:91-105.
Rawlings, et al., "Families of Serine Peptidases", Methods in Enzymology, Science Direct Elsevier B.V., 1994, 244:19-61 (publisher summary only).
Roointan, et al., "Road to the Future of Systems Biotechnology: CRISPR-Cas-Mediated Metabolic Engineering for Recombinant Protein Production", Biotechnology and Genetic Engineering Reviews, 2016, 32(1-2):74-91.

(Continued)

*Primary Examiner* — Maryam Monshipouri
(74) *Attorney, Agent, or Firm* — Grant IP, Inc.

(57) ABSTRACT

The present invention relates to a method for the recombinant production of a serine protease comprising (a) culturing a host cell comprising one or more vectors, wherein the one or more vectors encode in expressible form the serine protease and a proteinaceous inhibitor of the serine protease, wherein the proteinaceous inhibitor of the serine protease is heterologous with respect to the serine protease, under conditions wherein the serine protease and the proteinaceous inhibitor of the serine protease are expressed; or (a') culturing a host cell the genome of which encodes in expressible form the serine protease and a proteinaceous inhibitor of the serine protease, wherein the proteinaceous inhibitor of the serine protease is heterologous with respect to the serine protease, and wherein the coding sequences of the serine protease and/or the proteinaceous inhibitor have been introduced into the host cell genome by applying a CRISPR technology, under conditions wherein the serine protease and the proteinaceous inhibitor of the serine protease are expressed; and (b) isolating the serine protease expressed in step (a) or (a') from the host cell. The present invention also relates to a host cell comprising one or more vectors, wherein the one or more vectors encode in expressible form a serine protease and a proteinaceous inhibitor of the serine protease.

19 Claims, 5 Drawing Sheets
Specification includes a Sequence Listing.

(56) References Cited

OTHER PUBLICATIONS

Sakuma, et al., "Multiplex Genome Engineering in Human Cells Using All-in-one CRISPR/Cas9 Vector System", Scientific Reports, Jun. 23, 2014, 4(5400):6 pages.

Sander, et al., "CRISPR-Cas Systems for Editing, Regulating and Targeting Genomes", Nature Biotechnology, Apr. 2014, 32(4):347-355.

Shmakov, S., et al., "Discovery and Functional Characterization of Diverse Class 2 CRISPR-Cas Systems", Molecular Cell, Nov. 5, 2015, 60(3):385-397.

Tsuzuki, et al., "Evidence for the Occurrence of Membrane-Type Serine Protease 1/Matriptase on the Basolateral Sides of Enterocytes", Biochemical Journal, 2005, 388(Pt 2):679-687.

Vedvick, et al., "High-level Secretion of Biologically Active Aprotinin from the Yeast *Pichia pastoris*", Journal of Industrial Microbiology, Apr. 1991, 7(3):197-201.

Wladyka, et al., "Efficient Co-expression of a Recombinant Staphopain a and its Inhibitor Staphostatin a in *Escherichia coli*", Biochemical Journal, Jan. 2005, 385(1):181-187.

Yang, et al., "Expression and Purification of Natural N-Terminal Recombinant Bovine Pancreatic Trypsin Inhibitor from Pichia Pastoris", Biological and Pharmaceutical Bulletin, 2008, 31(9):1680-1685.

Zsebo, et al., "Protein Secretion from *Saccharomyces cerevisiae* Directed by the Prepro-alpha-factor Leader Region", Journal of Biological Chemistry, May 5, 1986, 261(13):5858-5865.

Communication pursuant to Rule 164(2)(b) and Article 94(3) EPC dated Mar. 25, 2021 received in European Application No. 18729899.7, 11 pages.

Franta et al., "Next Generation Sequencing Identifies Five Major Classes of Potentially Therapeutic Enzymes Secreted by Lucilia sericata Medical Maggots", BioMed Research International, 2016, 2016(8285428):27 pages.

\* cited by examiner a

ProDebrilase

Aprotinin

Early activated Debrilase -
Debrilase-Aprotinin-complex

Figure 4:
Figure 4:
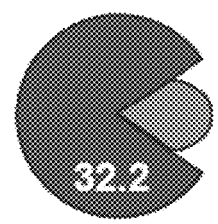
Figure 4:

Figure 4 – continued
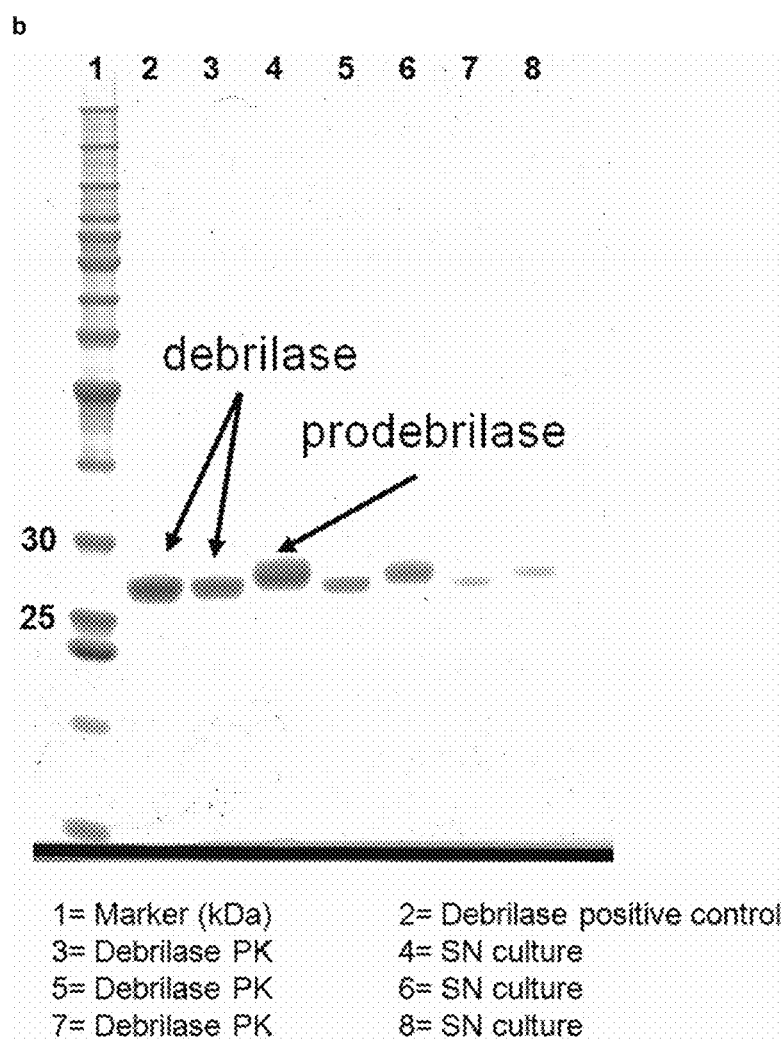

ns the EXPRESSION OF

```
SEQUENCE LISTING

<160> NUMBER OF SEQ ID NOS: 12

<210> SEQ ID NO 1
<211> LENGTH: 58
<212> TYPE: PRT
<213> ORGANISM: Bos taurus

<400> SEQUENCE: 1

Arg Pro Asp Phe Cys Leu Glu Pro Pro Tyr Thr Gly Pro Cys Lys Ala
1               5                   10                  15

Arg Ile Ile Arg Tyr Phe Tyr Asn Ala Lys Ala Gly Leu Cys Gln Thr
            20                  25                  30

Phe Val Tyr Gly Gly Cys Arg Ala Lys Arg Asn Asn Phe Lys Ser Ala
        35                  40                  45

Glu Asp Cys Met Arg Thr Cys Gly Gly Ala
    50                  55

<210> SEQ ID NO 2
<211> LENGTH: 177
<212> TYPE: DNA
<213> ORGANISM: Artificial Sequence
<220> FEATURE:
<223> OTHER INFORMATION: Codon-optimized nucleotide sequence of
      aprotinin

<400> SEQUENCE: 2
agaccagact tctgtttgga accaccatac actggtccat gtaaggctag aatcatcaga      60
tacttctaca acgctaaggc tggtttgtgt cagactttcg tttacggtgg ttgtagagct     120
aagagaaaca acttcaagtc cgctgaggac tgtatgagaa cttgtggtgg tgcttaa        177

<210> SEQ ID NO 3
<211> LENGTH: 254
<212> TYPE: PRT
```

<213> ORGANISM: Lucilia sericata

<400> SEQUENCE: 3

Met Phe Arg Phe Val Ala Leu Phe Ala Phe Val Ser Cys Ala Leu Ala
1               5                   10                  15

Gly Ala Ile Pro Asn Asp Leu Asp Gly Arg Ile Val Asn Gly Val Asp
            20                  25                  30

Thr Thr Ile Gln Ala His Pro Tyr Gln Val Ser Leu Gln Thr Asn Asn
        35                  40                  45

Gly Phe His Phe Cys Gly Gly Ser Ile Ile Ser Glu Asp Ile Ile Val
    50                  55                  60

Thr Ala Ala His Cys Met Gln Ser Tyr Lys Ala Tyr Gln Phe Lys Val
65                  70                  75                  80

Arg Leu Gly Ser Thr Glu Tyr Asp Asn Gly Gly Glu Leu Val Ala Val
                85                  90                  95

Lys Ser Phe Lys Tyr His Glu Gly Tyr Asn Pro Glu Thr Met Val Asn
            100                 105                 110

Asp Val Ala Val Ile Lys Leu Ala Thr Pro Val Arg Glu Ser Ser Lys
        115                 120                 125

Val Arg Tyr Val Lys Leu Ala Glu Lys Thr Pro Ala Thr Gly Thr Pro
    130                 135                 140

Ala Val Val Thr Gly Trp Gly Ser Lys Cys Phe Leu Phe Cys Gln Thr
145                 150                 155                 160

Ala Pro Lys Val Leu Gln Lys Val Glu Val Asp Ile Val Asp Glu Lys
                165                 170                 175

Thr Cys Ala Ser Ser Glu Tyr Lys Tyr Gly Asp Asp Ile Lys Glu Thr
            180                 185                 190

Met Leu Cys Ala Tyr Ala Val Lys Lys Asp Ala Cys Gln Gly Asp Ser
        195                 200                 205

Gly Gly Pro Leu Val Ala Asn Asn Lys Leu Val Gly Val Val Ser Trp
    210                 215                 220

Gly Lys Gly Cys Ala Leu Ala Gly Tyr Pro Gly Val Tyr Cys Asp Val
225                 230                 235                 240

Ala Thr Val Arg Ser Trp Ile Glu Lys Thr Ala Lys Ser Leu
                245                 250

<210> SEQ ID NO 4
<211> LENGTH: 238
<212> TYPE: PRT
<213> ORGANISM: Lucilia sericata

<400> SEQUENCE: 4

Gly Ala Ile Pro Asn Asp Leu Asp Gly Arg Ile Val Asn Gly Val Asp
1               5                   10                  15

Thr Thr Ile Gln Ala His Pro Tyr Gln Val Ser Leu Gln Thr Asn Asn
            20                  25                  30

Gly Phe His Phe Cys Gly Gly Ser Ile Ile Ser Glu Asp Ile Ile Val
        35                  40                  45

Thr Ala Ala His Cys Met Gln Ser Tyr Lys Ala Tyr Gln Phe Lys Val
    50                  55                  60

Arg Leu Gly Ser Thr Glu Tyr Asp Asn Gly Gly Glu Leu Val Ala Val
65                  70                  75                  80

Lys Ser Phe Lys Tyr His Glu Gly Tyr Asn Pro Glu Thr Met Val Asn
                85                  90                  95

Asp Val Ala Val Ile Lys Leu Ala Thr Pro Val Arg Glu Ser Ser Lys

```
            100                 105                 110
Val Arg Tyr Val Lys Leu Ala Glu Lys Thr Pro Ala Thr Gly Thr Pro
            115                 120                 125

Ala Val Val Thr Gly Trp Gly Ser Lys Cys Phe Leu Phe Cys Gln Thr
            130                 135                 140

Ala Pro Lys Val Leu Gln Lys Val Glu Val Asp Ile Val Asp Glu Lys
145                 150                 155                 160

Thr Cys Ala Ser Ser Glu Tyr Lys Tyr Gly Asp Asp Ile Lys Glu Thr
                165                 170                 175

Met Leu Cys Ala Tyr Ala Val Lys Lys Asp Ala Cys Gln Gly Asp Ser
            180                 185                 190

Gly Gly Pro Leu Val Ala Asn Asn Lys Leu Val Gly Val Ser Trp
            195                 200                 205

Gly Lys Gly Cys Ala Leu Ala Gly Tyr Pro Gly Val Tyr Cys Asp Val
            210                 215                 220

Ala Thr Val Arg Ser Trp Ile Glu Lys Thr Ala Lys Ser Leu
225                 230                 235
```

<210> SEQ ID NO 5
<211> LENGTH: 228
<212> TYPE: PRT
<213> ORGANISM: Lucilia sericata

<400> SEQUENCE: 5

```
Ile Val Asn Gly Val Asp Thr Thr Ile Gln Ala His Pro Tyr Gln Val
1               5                   10                  15

Ser Leu Gln Thr Asn Asn Gly Phe His Phe Cys Gly Gly Ser Ile Ile
            20                  25                  30

Ser Glu Asp Ile Ile Val Thr Ala Ala His Cys Met Gln Ser Tyr Lys
        35                  40                  45

Ala Tyr Gln Phe Lys Val Arg Leu Gly Ser Thr Glu Tyr Asp Asn Gly
    50                  55                  60

Gly Glu Leu Val Ala Val Lys Ser Phe Lys Tyr His Glu Gly Tyr Asn
65                  70                  75                  80

Pro Glu Thr Met Val Asn Asp Val Ala Val Ile Lys Leu Ala Thr Pro
                85                  90                  95

Val Arg Glu Ser Ser Lys Val Arg Tyr Val Lys Leu Ala Glu Lys Thr
            100                 105                 110

Pro Ala Thr Gly Thr Pro Ala Val Val Thr Gly Trp Gly Ser Lys Cys
            115                 120                 125

Phe Leu Phe Cys Gln Thr Ala Pro Lys Val Leu Gln Lys Val Glu Val
        130                 135                 140

Asp Ile Val Asp Glu Lys Thr Cys Ala Ser Ser Glu Tyr Lys Tyr Gly
145                 150                 155                 160

Asp Asp Ile Lys Glu Thr Met Leu Cys Ala Tyr Ala Val Lys Lys Asp
                165                 170                 175

Ala Cys Gln Gly Asp Ser Gly Gly Pro Leu Val Ala Asn Asn Lys Leu
            180                 185                 190

Val Gly Val Ser Trp Gly Lys Gly Cys Ala Leu Ala Gly Tyr Pro
            195                 200                 205

Gly Val Tyr Cys Asp Val Ala Thr Val Arg Ser Trp Ile Glu Lys Thr
            210                 215                 220

Ala Lys Ser Leu
225
```

<210> SEQ ID NO 6
<211> LENGTH: 765
<212> TYPE: DNA
<213> ORGANISM: Lucilia sericata

<400> SEQUENCE: 6

| | | | | | |
|---|---|---|---|---|---|
| atgttccggt | ttgtagctct | attcgctttc | gttagctgtg | ccttggcggg | cgctattccc | 60 |
| aatgatttgg | atggccgcat | tgtcaatggt | gtggatacca | ccattcaggc | ccatccctat | 120 |
| caggtttctt | tgcaaaccaa | caatggtttc | catttctgcg | gtggttccat | catcagcgaa | 180 |
| gacattattg | taactgctgc | tcattgcatg | caatcctaca | aggcctacca | attcaaagta | 240 |
| cgtttgggtt | ccactgaata | cgataatggt | ggtgaattgg | ttgccgtcaa | gtctttcaaa | 300 |
| taccacgaag | gttacaatcc | cgaaaccatg | gttaatgatg | ttgccgttat | caaattagcc | 360 |
| actccagtgc | gtgaatcttc | caaggtacgt | tatgttaaat | tggctgagaa | gacacctgct | 420 |
| actggcaccc | cagctgtcgt | tactggttgg | ggttctaagt | gcttcttgtt | ctgccaaact | 480 |
| gcccctaaag | ttttgcaaaa | ggttgaggtc | gatattgttg | atgagaagac | ctgcgcttcc | 540 |
| agcgaataca | aatatggtga | tgacatcaag | gaaactatgt | tgtgtgctta | tgctgttaag | 600 |
| aaggatgctt | gccaaggtga | ttctggtggt | cctttggttg | ccaacaacaa | attggtcggt | 660 |
| gttgtttcct | ggggtaaagg | ttgtgcccct | gctggctatc | ccggtgtata | ctgcgatgtt | 720 |
| gctactgtcc | gcagctggat | tgaaaagact | gccaagagtt | tgtaa | | 765 |

<210> SEQ ID NO 7
<211> LENGTH: 717
<212> TYPE: DNA
<213> ORGANISM: Lucilia sericata

<400> SEQUENCE: 7

| | | | | | |
|---|---|---|---|---|---|
| ggcgctattc | ccaatgattt | ggatggccgc | attgtcaatg | gtgtggatac | caccattcag | 60 |
| gcccatccct | atcaggtttc | tttgcaaacc | aacaatggtt | ccatttctg | cggtggttcc | 120 |
| atcatcagcg | aagacattat | tgtaactgct | gctcattgca | tgcaatccta | caaggcctac | 180 |
| caattcaaag | tacgtttggg | ttccactgaa | tacgataatg | gtggtgaatt | ggttgccgtc | 240 |
| aagtctttca | ataccacga | aggttacaat | cccgaaacca | tggttaatga | tgttgccgtt | 300 |
| atcaaattag | ccactccagt | gcgtgaatct | tccaaggtac | gttatgttaa | attggctgag | 360 |
| aagacacctg | ctactggcac | cccagctgtc | gttactggtt | ggggttctaa | gtgcttcttg | 420 |
| ttctgccaaa | ctgcccctaa | agttttgcaa | aaggttgagg | tcgatattgt | tgatgagaag | 480 |
| acctgcgctt | ccagcgaata | caaatatggt | gatgacatca | aggaaactat | gttgtgtgct | 540 |
| tatgctgtta | agaaggatgc | ttgccaaggt | gattctggtg | gtcctttggt | tgccaacaac | 600 |
| aaattggtcg | gtgttgtttc | ctggggtaaa | ggttgtgccc | ttgctggcta | tcccggtgta | 660 |
| tactgcgatg | ttgctactgt | ccgcagctgg | attgaaaaga | ctgccaagag | tttgtaa | 717 |

<210> SEQ ID NO 8
<211> LENGTH: 687
<212> TYPE: DNA
<213> ORGANISM: Lucilia sericata

<400> SEQUENCE: 8

| | | | | | |
|---|---|---|---|---|---|
| attgtcaatg | gtgtggatac | caccattcag | gcccatccct | atcaggtttc | tttgcaaacc | 60 |
| aacaatggtt | ccatttctg | cggtggttcc | atcatcagcg | aagacattat | tgtaactgct | 120 |
| gctcattgca | tgcaatccta | caaggcctac | caattcaaag | tacgtttggg | ttccactgaa | 180 |

```
tacgataatg gtggtgaatt ggttgccgtc aagtctttca aataccacga aggttacaat      240
cccgaaacca tggttaatga tgttgccgtt atcaaattag ccactccagt gcgtgaatct      300
tccaaggtac gttatgttaa attggctgag aagacacctg ctactggcac cccagctgtc      360
gttactggtt ggggttctaa gtgcttcttg ttctgccaaa ctgcccctaa agttttgcaa      420
aaggttgagg tcgatattgt tgatgagaag acctgcgctt ccagcgaata caaatatggt      480
gatgacatca aggaaactat gttgtgtgct tatgctgtta agaaggatgc ttgccaaggt      540
gattctggtg gtccttggt tgccaacaac aaattggtcg gtgttgtttc ctggggtaaa      600
ggttgtgccc ttgctggcta tcccggtgta tactgcgatg ttgctactgt ccgcagctgg      660
attgaaaaga ctgccaagag tttgtaa                                          687
```

```
<210> SEQ ID NO 9
<211> LENGTH: 60
<212> TYPE: PRT
<213> ORGANISM: Artificial Sequence
<220> FEATURE:
<223> OTHER INFORMATION: Aprotinin fused to EA-Tag

<400> SEQUENCE: 9

Glu Ala Arg Pro Asp Phe Cys Leu Glu Pro Pro Tyr Thr Gly Pro Cys
1               5                   10                  15

Lys Ala Arg Ile Ile Arg Tyr Phe Tyr Asn Ala Lys Ala Gly Leu Cys
            20                  25                  30

Gln Thr Phe Val Tyr Gly Gly Cys Arg Ala Lys Arg Asn Asn Phe Lys
        35                  40                  45

Ser Ala Glu Asp Cys Met Arg Thr Cys Gly Gly Ala
    50                  55                  60
```

```
<210> SEQ ID NO 10
<211> LENGTH: 183
<212> TYPE: DNA
<213> ORGANISM: Artificial Sequence
<220> FEATURE:
<223> OTHER INFORMATION: Aprotinin fused to GAAGCT-Tag

<400> SEQUENCE: 10
gaagctagac cagacttctg tttggaacca ccatacactg gtccatgtaa ggctagaatc      60
atcagatact tctacaacgc taaggctggt ttgtgtcaga ctttcgttta cggtggttgt     120
agagctaaga gaaacaactt caagtccgct gaggactgta tgagaacttg tggtggtgct     180
taa                                                                   183
```

```
<210> SEQ ID NO 11
<211> LENGTH: 438
<212> TYPE: DNA
<213> ORGANISM: Artificial Sequence
<220> FEATURE:
<223> OTHER INFORMATION: Aprotinin sequence fused to sequence of the
      alpha mating factor from S. cerevisiae

<400> SEQUENCE: 11
atgagattcc catctatttt caccgctgtc ttgttcgctg cctcctctgc attggctgcc      60
cctgttaaca ctaccactga agacgagact gctcaaattc cagctgaagc agttatcggt     120
tactctgacc ttgagggtga tttcgacgtc gctgttttgc cttctctaa ctccactaac     180 aacggtttgt tgttcattaa caccactatc gcttccattg ctgctaagga agagggtgtc     240
tctctcgaga aaagagaagc tagaccagac ttctgtttgg aaccaccata cactggtcca     300
```

```
tgtaaggcta gaatcatcag atacttctac aacgctaagg ctggtttgtg tcagactttc    360
gtttacggtg gttgtagagc taagagaaac aacttcaagt ccgctgagga ctgtatgaga    420
acttgtggtg gtgcttaa                                                   438
```

<210> SEQ ID NO 12
<211> LENGTH: 145
<212> TYPE: PRT
<213> ORGANISM: Artificial Sequence
<220> FEATURE:
<223> OTHER INFORMATION: Aprotinin sequence fused to sequence of the
      alpha mating factor from S. cerevisiae

<400> SEQUENCE: 12

```
Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Glu Lys Arg Glu Ala Arg Pro Asp Phe Cys Leu Glu Pro Pro
                85                  90                  95

Tyr Thr Gly Pro Cys Lys Ala Arg Ile Ile Arg Tyr Phe Tyr Asn Ala
            100                 105                 110

Lys Ala Gly Leu Cys Gln Thr Phe Val Tyr Gly Gly Cys Arg Ala Lys
        115                 120                 125

Arg Asn Asn Phe Lys Ser Ala Glu Asp Cys Met Arg Thr Cys Gly Gly
    130                 135                 140

Ala
145
```

OPTIMIZATION OF THE EXPRESSION OF SERINE PROTEASES IN HOST CELLS

RELATED PATENT APPLICATIONS

This patent application is a 35 U.S.C. 371 national phase patent application of PCT/EP2018/064216, filed on May 30, 2018, entitled "OPTIMIZATION OF THE EXPRESSION OF SERINE PROTEASES IN HOST CELLS", naming Alexander Pelzer and Bela Kelety as inventors, which claims priority to European Application No. 17173813.1 filed on May 31, 2017, entitled "OPTIMIZATION OF THE EXPRESSION OF SERINE PROTEASES IN HOST CELLS," naming Alexander Pelzer and Bela Kelety as inventors. The entire content of the foregoing patent applications is incorporated herein by reference, including all text, tables and drawings.

SEQUENCE LISTING

The instant application contains a Sequence Listing which has been submitted electronically in ASCII format and is hereby incorporated by reference in its entirety. Said ASCII copy is named AA1177US_sequence_listing and is 13.2 kilobytes in size.

The present invention relates to a method for the recombinant production of a serine protease comprising (a) culturing a host cell comprising one or more vectors, wherein the one or more vectors encode in expressible form the serine protease and a proteinaceous inhibitor of the serine protease, wherein the proteinaceous inhibitor of the serine protease is heterologous with respect to the serine protease, under conditions wherein the serine protease and the proteinaceous inhibitor of the serine protease are expressed; or (a') culturing a host cell the genome of which encodes in expressible form the serine protease and a proteinaceous inhibitor of the serine protease, wherein the proteinaceous inhibitor of the serine protease is heterologous with respect to the serine protease, and wherein the coding sequences of the serine protease and/or the proteinaceous inhibitor have been introduced into the host cell genome by applying a CRISPR technology, under conditions wherein the serine protease and the proteinaceous inhibitor of the serine protease are expressed; and (b) isolating the serine protease expressed in step (a) or (a') from the host cell. The present invention also relates to a host cell comprising one or more vectors, wherein the one or more vectors encode in expressible form a serine protease and a proteinaceous inhibitor of the serine protease.

In this specification, a number of documents including patent applications and manufacturer's manuals are cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

The recombinant production of proteins in host cell systems has revolutionized biochemistry since large amounts of animal and/or plant tissues or large volumes of biological fluids are no longer needed for the production of a large quantity of a given protein. The ability to produce a desired protein in a large quantity allows for its biochemical characterization, its use in industrial processes and the development of commercial goods. While most desired proteins can be conveniently produced in host cells certain proteins or classes of proteins are still challenging to produce, in particular in large amounts.

One example of such a class of proteins is proteases, wherein one major problem is the self-degrading activity of proteases during heterologous expression in a host cell. It is therefore state of the art to express proteases in their naturally-occurring inactive form as proenzymes with subsequent activation when appropriate. However, also the expression of the proteases as proenzyme does not totally overcome the problem. There is still undesirable activation of the protease by proteolytic (self)cleavage of the propeptide which inter alia leads to an unwanted cascade of enzyme degradation within the host cell. This enzyme degradation damages the host cell and thereby the production yield of the protease.

In the prior art some examples of expressing in a host cell a protease together with its natural protease inhibitors have been described in order to prevent the undesirable activation of the protease by proteolytic (self)cleavage. For instance, the expression of the protein matrix-metalloproteinase (MMP) in the presence of its inhibitor (MMPI) is described in WO 1998/012211. Another example is the recombinant co-expression of the cysteine endopeptidase staphopain A and its inhibitor staphostatin A in *E. coli* (see Wladyka et al. (2005), Biochem J., 385, 181-187). However, the natural protease inhibitors are not known for each and every protease. In addition, no such expression system has been successfully established for a serine protease.

Hence, the technical problem underlying the present invention is the provision of improved means and methods for the recombinant production of virtually any serine protease in a host cell, and in particular means and methods for further increasing the yields of the serine protease to be recombinantly produced.

Accordingly the present invention relates in first aspect to a method for the recombinant production of a serine protease comprising (a) culturing a host cell comprising one or more vectors, wherein the one or more vectors encode in expressible form the serine protease and a proteinaceous inhibitor of the serine protease, wherein the proteinaceous inhibitor of the serine protease is heterologous with respect to the serine protease, under conditions wherein the serine protease and the proteinaceous inhibitor of the serine protease are expressed; or (a') culturing a host cell the genome of which encodes in expressible form the serine protease and a proteinaceous inhibitor of the serine protease, wherein the proteinaceous inhibitor of the serine protease is heterologous with respect to the serine protease, and wherein the coding sequences of the serine protease and/or the proteinaceous inhibitor have been introduced into the host cell genome by applying a CRISPR technology, under conditions wherein the serine protease and the proteinaceous inhibitor of the serine protease are expressed; and (b) isolating the serine protease expressed in step (a) or (a') from the host cell.

The present invention also relates to a method for the recombinant production of a serine protease comprising (a') introducing one or more vectors into a host cell, wherein the one or more vectors encode in expressible form the serine protease and a proteinaceous inhibitor of the serine protease, wherein the proteinaceous inhibitor of the serine protease is heterologous with respect to the serine protease; or (a") introducing into a host cell one or more nucleic acid molecules encoding in expressible form (i) a CRISPR nuclease, (ii) a guide RNA for inserting the serine protease and/or a guide RNA for inserting a proteinaceous inhibitor of the serine protease into the genome of the host cell, wherein the proteinaceous inhibitor of the serine protease is heterologous with respect to the serine protease, (a) culturing the host cell of ($a^i$) or ($a^{ii}$) under conditions wherein the serine protease and the proteinaceous inhibitor of the serine protease are expressed; and (b) isolating the serine protease expressed in step (a) from the host cell.

Instead of introducing into a host cell one or more nucleic acid molecules encoding in expressible form a CRISPR nuclease it is also possible to introduce the CRISPR nuclease as a protein. Means for introducing proteins into living cells are known in the art. They include methods for introducing a protein directly into a cell which are well known in the state of the art and comprise but are not limited to microinjection, electroporation, lipofection (using liposomes), nanoparticle-based delivery, and protein transduction. The CRISPR nuclease may be introduced into the cells as an active enzyme or as a proenzyme. In the latter case the CRISPR nuclease is biochemically changed within the cells (for example by a hydrolysis reaction revealing the active site, or changing the configuration to reveal the active site), so that the proenzyme becomes an active enzyme.

In general terms the recombinant expression of a serine protease designates a biotechnological process of generating the serine protease. This is typically achieved by the manipulation of the gene expression in a host cell, so that the host cell expresses significant amounts of the recombinant gene (i.e. mRNA) encoding the serine protease. The mRNA is then translated into an amino acid sequence being further processed within the host cell into the serine protease in the form wherein it can be isolated from the host cell.

The term "serine protease" characterizes a protein having in its mature enzymatically active form proteolytic activity which belongs to a subgroup the members of which comprise a serine in their active centre which together with histidine and aspartate forms the catalytic triad common to most serine proteases (Rawlings, N. D., Barrett, A. J. (1994), Families of serine peptidases. *Meth. Enzymol.* 244:19-61). Serine-proteases are classified as hydrolases. They are found ubiquitously in both eukaryotes and prokaryotes. Three major classes have been defined based on the physicochemical properties of the P1 site, trypsin-like (positively charged residues Lys/Arg preferred at P1), elastase-like (small hydrophobic residues Ala, Val at P1) or chymotrypsin-like (large hydrophobic residues Phe/Tyr/Leu at P1) serine proteases. With respect to the designation P1 it is of note that a general nomenclature of cleavage site positions of substrates was formulated by Schechter and Berger in 1967-68. The cleavage site positions designate the cleavage site between P1-P1', incrementing the numbering in the N-terminal direction of the cleaved peptide bond (P2, P3, P4, etc.). On the carboxyl side of the cleavage site the numbering is incremented in the same way (P1', P2', P3' etc.). The serine protease of the present invention is preferably a chymotrypsin-like or trypsin-like serine protease, and more preferably a trypsin-like serine protease.

Serine proteases are generally initially produced in the host cell in the form of a pre-proprotein. The pre-proprotein is the primary translation product. The prefix "pre-" designates that the protein is initially produced within the host with an N-terminal signal peptide that targets the serine protease for secretion. Said signal peptide is cleaved-off during a secretion process e.g. in the endoplasmatic reticulum of the host cell. The signal peptide is a short amino acid sequence (preferably, 3-60 amino acids long). By this cleavage the pre-proprotein is transformed into the proprotein of the serine protease. The proprotein is substantially enzymatically inactive. Albeit a part of the proprotein is-cleaved and thereby becomes active in the host cell, this proprotein is the major form in which the serine protease is produced in accordance with the method of the first aspect of the invention. The proprotein may be enzymatically processed into the mature protein (i.e. enzymatically active protein) by cleaving the propeptide (or also being designated inhibitory peptide) from the proprotein. In more detail, the activation of many serine proteases, in particular many trypsin-like serine proteases require proteolytically processing an enzymatically inactive proprotein precursor. Hence, in accordance with the present invention the term "serine protease" refers to and includes all three forms of a serine protease the pre-proprotein, the proprotein and the mature protein.

The term "proteinaceous inhibitor of a serine protease" or "proteinaceous serine protease inhibitor" characterizes a protein or peptide having the ability to inhibit the proteolytic activity of a serine protease. There are two types of trypsin inhibitors: the Kunitz trypsin inhibitors (KTI) and the Bowman-Birk inhibitors (BBI). The Bowman-Birk protease inhibitor family of proteins is mainly found in plants and these proteins inhibit serine peptidases of the S1 family, but also inhibit S3 peptidases. They consist of eukaryotic proteinase inhibitors, belonging to MEROPS inhibitor family I12, clan IF. The members of the other group of proteinaceous serine protease inhibitors are a well-defined class of molecules usually and preferably being characterized by the presence of a Kunitz domain (InterPro identifier IPR002223). A Kunitz domain is relatively small with a length of about 50 to 60 amino acids and a molecular weight of about 6 kDa. The structure of a Kunitz domain comprises a disulfide rich alpha/beta-fold. The fold is constrained by 3 disulphide bonds. The basic structure of a Kunitz domain is preferably xxCxxC #xxxCxxxCxxxxxxCxxxxCxx, wherein the 'Cs' are conserved cysteines involved in disulfide bonds, and '#' is the active site amino acid residue. Examples of Kunitz-type protease inhibitors are aprotinin (bovine pancreatic trypsin inhibitor, BPTI), snake venom basic protease, mammalian inter-alpha-trypsin inhibitors, trypstatin (a rodent mast cell inhibitor of trypsin), a domain found in an alternatively-spliced form of Alzheimer's amyloid beta-protein, domains at the C-termini of the alpha(1) and alpha (3) chains of type VII and type VI collagens, and tissue factor pathway inhibitor precursor.

For example, phenylmethylsulfonyl fluoride (PMSF) and 4-amidinophenylmethylsulfonyl fluoride (APMSF) are universal non-proteinaceous serine protease inhibitors which are, for example, commonly used in the preparation of cell lysates. PMSF and APMSF covalently bind to the active site serine residue in a serine protease, whereby an irreversible enzyme-(A)PMS complex is generated. Non-proteinaceous serine protease inhibitors, such as PMSF and APMSF are chemical molecules being structurally distinct from the proteinaceous serine protease inhibitors of the invention.

Proteinaceous serine protease inhibitors can work in different ways to inhibit the action of a serine protease. Reversible inhibitors usually bind to the protease with multiple non-covalent interactions, without any reaction of the inhibitor itself. These inhibitors can be removed by dilution or dialysis. Reversible inhibitors include competitive inhibitors, uncompetitive inhibitors, and non-competitive inhibitors. Competitive inhibitors bind to the active site of the protease, competing with substrates for access to the active site residues. One example of a competitive inhibitor is aprotinin. Competitive inhibitors are often similar in structure to the transition state of natural substrates. The transition state of the substrate is the structure that binds most tightly with the serine protease. Therefore, compounds mimicking this structure bind to the serine protease with a greater strength than the substrate (in its initial state) can, and the normal enzymatic reaction cannot proceed. Uncompetitive inhibitors bind only to the protease when it is already bound to a substrate. Non-competitive inhibitors bind to the serine protease, with or without bound substrate, with similar affinities, and inhibit serine protease activity through an allosteric mechanism. For example, BBI, a trypsin inhibitor from soybean is a non-competitive inhibitor. Irreversible inhibitors function by specifically altering the active site of its specific target through covalent bond formation. Upon binding to the inhibitor, the serine protease's active site is altered, and it can no longer perform peptide bond hydrolysis. Some inhibitors do not covalently bind to the protease, but interact with such a high affinity, that they are not easily removed. Suicide inhibitors, being typically analogues of the substrate, are a type of irreversible inhibitor that covalently binds to the serine protease. An example of a suicide serine protease inhibitor is the serpin family of proteins, which play a role in blood coagulation and inflammation. The proteinaceous serine protease inhibitor of the present invention is preferably a reversible inhibitor and more preferably a reversible and competitive inhibitor.

The proteinaceous inhibitor of a serine protease is in accordance with the invention heterologous with respect to the serine protease. This means that the proteinaceous inhibitor of a serine protease and the serine protease are not naturally expressed in the same species. Moreover, the proteinaceous inhibitor of a serine protease is more preferably not a natural inhibitor of the serine protease including any species orthologs of the serine protease. The term "protein", alternatively used to the term "polypeptide" as used herein describes linear molecular chains of amino acids, including single chain proteins or their fragments, preferably containing more than 30 amino acids. An amino acid stretch of 30 amino acids and less than 30 amino acids would normally only be termed "peptide". Depending on the circumstances, the term "protein" herein may denote the mature protein, the proprotein of the mature protein or the pre-proprotein of the mature protein. Proteins may further form oligomers consisting of at least two identical or different molecules. The corresponding higher order structures of such multimers are, correspondingly, termed homo- or heterodimers, homo- or heterotrimers etc. Furthermore, peptidomimetics of such proteins where amino acid(s) and/or peptide bond(s) have been replaced by functional analogues are also encompassed by the invention. Such functional analogues include all known amino acids other than the 20 gene-encoded amino acids, such as selenocysteine. The terms "protein" and "peptide" also refer to naturally modified proteins and peptides where the modification is effected e.g. by glycosylation, acetylation, phosphorylation and similar modifications which are well known in the art.

The host cell can be a prokaryotic host cell or a eukaryotic host cell, the latter including fungal, insect, yeast and mammalian host cells.

Suitable prokaryotic host cells comprise e.g. bacteria of the species *Escherichia*, such as strains derived from *E. coli* BL21 (e.g. BL21(DE3), BL21(DE3)PlysS, BL21(DE3)RIL, BL21(DE3)PRARE, BL21 codon plus, BL21(DE3) codon plus), Rosetta®, XL1 Blue, NM522, JM101, JM109, JM105, RR1, DH5α, TOP 10, HB101 or MM294. Further suitable bacterial host cells are *Streptomyces, Salmonella* or *Bacillus* such as *Bacillus subtilis*. *E. coli* strains are preferred prokaryotic host cells in connection with the present invention.

Suitable eukaryotic host cells are e.g. yeasts such as *Saccharomyces cerevisiae, Hansenula polymorpha* or *Pichia* sp. such as *P. pastoris*, insect cells such as *Drosophila* S2 or *Spodoptera* Sf9 cells, or plant cells. Other suitable eukaryotic host cells are *Aspergillus* spec. cells, such that *Aspergillus niger* cells.

Mammalian host cells that could be used include human Hela, HEK293, H9 and Jurkat cells, mouse NIH3T3 and C127 cells, COS 1, COS 7 and CV1, quail QC1-3 cells, mouse L cells, Bowes melanoma cells and Chinese hamster ovary (CHO) cells.

Suitable conditions for culturing a prokaryotic or eukaryotic host cell, so that the serine protease and the inhibitor thereof are expressed are well known to the person skilled in the art. For example, suitable conditions for culturing bacteria are growing them under aeration in Luria Bertani (LB) medium. To increase the yield and the solubility of the expression product, the medium can be buffered or supplemented with suitable additives known to enhance or facilitate both. *E. coli* can typically be cultured from 4 to about 37° C., the exact temperature or sequence of temperatures depends on the molecule to be overexpressed. In general, the skilled person is also aware that these conditions may have to be adapted to the needs of the host and the requirements of the polypeptide expressed. In case an inducible promoter controls the nucleic acid of the invention in the vector present in the host cell, expression of the protein can be induced by addition of an appropriate inducing agent. Suitable expression protocols and strategies are known to the skilled person.

Depending on the host cell and its specific requirements, mammalian cell culture can e.g. be carried out in RPMI or DMEM medium containing 10% (v/v) FCS, 2 mM L-glutamine and 100 U/ml penicillin/streptomycin. The cells can be kept at 37° C. in a 5% $CO_2$, water saturated atmosphere.

Suitable media for insect cell culture is e.g. TNM+10% FCS or SF900 medium. Insect cells are usually grown at 27° C. as adhesion or suspension culture.

Suitable expression protocols for eukaryotic cells are well known to the skilled person and can be retrieved e.g. from Sambrook et al., (2012), Molecular cloning: a laboratory manual, 4th ed., Cold Spring Harbor Laboratory Press, New York.

As used herein the term "one or more vectors" refers to one or more nucleic acid (e.g. DNA) molecules used as a vehicle to artificially carry recombinant genetic material into a host cell, where it can be expressed. As defined herein, the recombinant genetic material comprises the nucleic acid(s) encoding the serine protease and a proteinaceous inhibitor of the serine protease. Within the one or more vectors the nucleic acid sequences encoding the serine protease the proteinaceous inhibitor of the serine protease can be organized in the same expression cassette or in two different expression cassettes. The term "expression cassette" as used herein refers to a nucleic acid molecule forming an integral part of the vector and encompassing nucleic sequences which are capable of directing expression of a nucleic acid sequence encoding the serine protease and/or the proteinaceous inhibitor thereof. An expression cassette in general comprises a promoter sequence, a gene encoding the protein to be produced and a terminator sequence, wherein the promoter sequence initiates expression while the terminator sequence terminates expression. In case the one or more vectors comprise two or more expression cassettes the nucleic sequences which are capable of directing expression may be the same or different among the expression cassettes.

It follows that in accordance with the present invention the one or more vectors may comprise or consist of (i) one vector comprising one expression cassette, said expression cassette being capable of directing the expression of a nucleic acid encoding the serine protease and the proteinaceous inhibitor thereof, (ii) one vector comprising two expression cassettes, wherein the first expression cassette is capable of directing the expression of a nucleic acid sequence encoding the serine protease and the second expression cassette is capable of directing the expression of a nucleic acid sequence encoding the proteinaceous inhibitor of the serine protease, or (iii) two vectors each comprising one expression cassette, wherein the expression cassette in the first vector is capable of directing the expression of a nucleic acid sequence encoding the serine protease and the expression cassette in the second vector is capable of directing the expression of a nucleic acid sequence encoding the proteinaceous inhibitor of the serine protease. Among these options (i) to (iii), options (ii) and (iii) are preferred and option (iii) is most preferred.

The vector may be an episomal vector or a chromosomal integration vector. Episomal vectors (or episome vectors or non-integrating vectors) as used herein designate vectors that autonomously replicate in the host cells and that stay extrachromosomally. By contrast, chromosomal integrating vectors (or integrating vectors) become integrated into the chromosomal DNA of the host cell thereby becoming a stable part of the host cell genome. Integrating vectors can be used to achieve long-term gene expression in a host cell. In this respect it is to be understood that at least the entire expression cassette(s) of the one or more vectors preferably become integrated into the host genome, so that the entire expressional control of the nucleic acid(s) encoding the serine protease and the proteinaceous inhibitor thereof is maintained after integration.

In a preferred embodiment the vector is a plasmid, cosmid, virus, bacteriophage or another vector used conventionally e.g. in genetic engineering. The nucleic acid sequence encoding the serine protease and/or the proteinaceous inhibitor of the present invention may be inserted into several commercially available vectors. This nucleic acid sequence may also be inserted into vectors such that a translational fusion with another nucleic acid molecule is generated. The other nucleic acid molecules may encode a protein that facilitates the purification of the serine protease of the present invention. Non-limiting examples of such vectors include pET32, pET41, pET43. The vectors may also contain an additional expressible polynucleotide coding for one or more proteins (e.g. chaperones) to facilitate correct protein folding.

For vector modification techniques, see Sambrook and Russel, 2001, Molecular Cloning, 4th ed. CSH Press. Generally, vectors can contain one or more origins of replication (on) and inheritance systems for cloning or expression, one or more markers for selection in the host, e.g., antibiotic resistance, and one or more expression cassettes. Suitable origins of replication include, for example, the Col E1, the SV40 viral and the M 13 origins of replication. The coding sequences inserted in the vector can e.g. be synthesized by standard methods, or isolated from natural sources. Ligation of the coding sequences to transcriptional regulatory elements and/or to other amino acid encoding sequences can be carried out using established methods. Transcriptional regulatory elements (parts of an expression cassette) ensuring expression in host cells are well-known to those skilled in the art. These elements comprise regulatory sequences ensuring the initiation of transcription (e.g., translation initiation codon, promoters, such as naturally-associated or heterologous promoters and/or insulators). Additional regulatory elements may include transcriptional as well as translational enhancers. Preferably, the nucleic acid sequence encoding the serine protease and/or the proteinaceous inhibitor of the present invention is operatively linked to such expression control sequences allowing expression in a host cell. The vector may further comprise a selectable marker. Examples of selectable markers include neomycin, ampicillin, chloramphenicol, hygromycine, gentamicin, kanamycin, rifampicin resistance and the like. Selectable marker genes for mammalian cell culture include the dhfr, gpt, neomycin, hygromycin resistance genes. The transfected nucleic acid can also be amplified to express large amounts of the encoded (poly)peptide. The DHFR (dihydrofolate reductase) marker is useful to develop cell lines that carry several hundred or even several thousand copies of the gene of interest. Another useful selection marker is the enzyme glutamine synthase (GS) (Murphy et al. 1991; Bebbington et al. 1992). Using such markers, the cells are grown in selective medium and the cells with the highest resistance are selected.

Non-limiting examples of vectors include prokaryotic plasmid vectors, such as the pUC-series, pBluescript (Stratagene), the pET-series of expression vectors (Novagen) or pCRTOPO (Invitrogen), lambda gt11, pJOE, the pBBR1-MCS series, pJB861, pBSMuL, pBC2, pUCPKS, pTACT1 and vectors compatible with expression in mammalian cells like E-027 pCAG Kosak-Cherry (L45a) vector system, pREP (Invitrogen), pCEP4 (Invitrogen), pMC1 neo (Stratagene), pXT1 (Stratagene), pSG5 (Stratagene), EBO-pSV2neo, pBPV-1, pdBPVMMTneo, pRSVgpt, pRSVneo, pSV2-dhfr, pIZD35, Okayama-Berg cDNA expression vector pcDV1 (Pharmacia), pRc/CMV, pcDNA1, pcDNA3 (Invitrogene), pSPORT1 (GIBCO BRL), pGEMHE (Promega), pLXIN, pSIR (Clontech), pIRES-EGFP (Clontech), pEAK-10 (Edge Biosystems) pTriEx-Hygro (Novagen) and pCI-Neo (Promega). Non-limiting examples of specific bacterial expression vectors that can be used herein are pACYC177, pASK75, pBAD/His A, pBAD/His B, pBAD/His C, pBAD/MCS, pBADM-11, pBADM-20, pBADM-20(+), pBADM-30, pBADM-30(+), pBADM-41(+), pBADM-52, pBADM-52(+), pBADM-60, pBADM-60(+), pBAT4, pBAT5, pCal-n, pET-3a, pET-3b, pET-3c, pET-3d, pET-12a, pET-14b, pET-15b, pET-16b, pET-19b, pET-20b(+), pET-21d(+), pET-22b(+), pET-24d(+), pET-28a, pET-28c, pET-32a(+), pET-32b(+), pET-32c(+), pET-39b(+), pET-40b(+), pETM-10, pETM-11, pETM11-SUMO3GFP, pETM-12, pETM-13, pETM-14, pETM-14_ccdB, pETM-20, pETM-21, pETM-22, pETM-22_ccdB, pETM-30, pETM-33, pETM-33_ccdB, pETM-40, pETM-41, pETM-43, pETM-44, pETM-44_ccdB, pETM-50, pETM-51, pETM-52, pETM-54, pETM-55, pETM-60, pETM-66, pETM-70, pETM-80, pETM-82, pGAT, pGAT2, pGEX-3X, pGEX-4T-1, pGEX-4T-2, pGEX-4T-3, pGEX-5X-1, pGEX-5X-2, pGEX-5X-3, pGEX-6P-1, pGEX-6P-2, pGEX-6P-3, pHAT, pHAT2, pKK223-3, pKK223-2, pMal-c2, pMal-p2, pProEx HTa, pProEx HTb, pProEx HTc, pQE-16, pQE-30, pQE-31, pQE-32, pQE-60, pQE-70, pQE-80L, pQE-81L, pQE-82L, pRSET A, pRSET B, pRSET C, pTrcHis2 A, pTrcHis2 B, pTrcHis2 C, pTrcHis2LacZ, pZA31-Luc, pZE12-Luc, pZE21-MCS-1, and pZS*24-MCS-1. Another vector suitable for expressing proteins in *xenopus* embryos, zebrafish embryos as well as a wide variety of mammalian and avian cells is the multipurpose expression vector pCS2+.

Yeast expression vectors that can be used in connection with the present invention are known in the art. Examples of yeast expression vectors for *Pichia* are the pPIC series or pHIL series of vectors. The pPIC vectors generally use the AOX1 promoter which is inducible with methanol. Examples for plasmid vectors suitable for *Pichia pastoris* comprise e.g. the plasmids pAO815, pPIC9K and pPIC3.5K (all Invitrogen).

Methods for introducing the one or more vectors into the host cell are well known to the skilled person and, for example, described in Sambrook et al., (2012), Molecular cloning: a laboratory manual, 4th ed., Cold Spring Harbor Laboratory Press, New York. Non-limiting examples are transduction, transformation, conjugation or transfection. Transformation is the process by which a donor DNA molecule is taken up from the external environment and incorporated into the genome of the recipient cell. Transduction involves transfer of genetic material from one bacterium to another by a bacteriophage. Acting as a vector, the phage carries its own genome plus a fragment of DNA from the bacterium it has recently infected. If the host bacterium survives the viral attack, recombination may occur. Conjugation is the temporary direct contact between two bacterial cells leading to an exchange of DNA. This exchange is unidirectional, i.e. one bacterial cell is the donor of DNA and the other is the recipient. In this way, genes are transferred laterally amongst existing bacterial as opposed to vertical gene transfer in which genes are passed on to offspring. Transfection is the process of deliberately introducing naked or purified nucleic acids by non-viral methods into cells. Transfection can, inter alia, be carried out using calcium phosphate (i.e. tricalcium phosphate), by electroporation, by cell squeezing or by mixing a cationic lipid with the material to produce liposomes which fuse with the cell membrane and deposit their cargo inside. For the transformation of prokaryotic cells $CaCl_2$ and heat shock or electroporation are frequently used in the art. For the transformation of yeast cells lithium-acetate, electroporation, spheroplasts, biolistics, and glass beads are frequently used in the art.

In an embodiment genome editing by CRISPR technology can be applied for stable modulation of gene expression and/or site-specific integration using class II cas-nucleases, such as cas9 or cpf1 (Shmakov et al. (2015) Discovery and Functional Characterization of Diverse Class 2 CRISPR-Cas Systems. Mol Cell. 2015 Nov. 5; 60(3):385-97).

In this embodiment a host cell is used that has been genome edited by CRISPR technology and encodes in expressible form the serine protease and a heterologous proteinaceous inhibitor of the serine protease. The genome editing may also form part of the method of the invention. In this case one or more nucleic acid molecules encoding in expressible form (i) (optionally) a CRISPR nuclease, (ii) a guide RNA for inserting the serine protease and a guide RNA for inserting a proteinaceous inhibitor of the serine protease into the genome of a host cell are introduced into the host cell. The one or more nucleic acid molecules can be one or more vectors as described herein below.

Genome editing (also known as genome engineering) uses in accordance with the invention the nucleases of the clustered regularly interspaced short palindromic repeats (CRISPR/Cas) system (also called herein CRISPR nucleases). Genome editing is a type of genetic engineering in which a gene of interest can be inserted, deleted, modified or replaced in the genome of the cell. Herein, genome editing is used to insert the genes introduce the genes encliding in expressible form a serine protease and a proteinaceous inhibitor of the serine protease intio to genome of a host cell.

The CRISPR-Cas system has been harnessed for genome editing in prokaryotes and eukaryotes. A small piece of RNA with a short "guide" sequence that attaches (binds) to a specific target sequence of DNA in a genome is created (the so-called guide RNA (gRNA) or single guide (sgRNA)). The genomic target site of the gRNA can be any ~20 nucleotide DNA sequence, provided it meets two conditions: (i) The sequence is unique compared to the rest of the genome, and (ii) the target is present immediately adjacent to a Protospacer Adjacent Motif (PAM). The PAM sequence is essential for target binding, but the exact sequence depends on which CRISPR endonuclease is used. CRISPR endonuclease and their respective PAM sequences are known in the art (see World Wide Web Uniform Resource Locator addgene.org/crispr/guide/#pam-table). Hence, the gRNA also binds to the CRISPR endonuclease (e.g. the Cas9 or Cpf1 enzyme). As in bacteria, the gRNA is used to recognize the DNA sequence, and the CRISPR endonuclease cuts the DNA at the targeted location. Once the DNA is cut, the cell's own DNA repair machinery (NHEJ or HDR) adds or deletes pieces of genetic material, or makes changes to the DNA by replacing an existing segment with a customized DNA sequence. Thus, in the CRISPR-Cas system, the CRISPR nuclease makes a double-stranded break in DNA at a site determined by the short (~20 nucleotide) gRNA which break is then repaired within the cell by NHEJ or HDR. The CRISPR-Cas system can be multiplexed by adding multiple gRNAs. It was demonstrated that, for example, five different simultaneous mutations can be introduced into mouse embryonic stem cells by using five different gRNA molecules and one CRISPR endonuclease; see Sanders and Young, Nat Biotechnol. 2014 April; 32(4): 347-355.

The nucleic acid molecules used for genome editing may be inserted into several commercially available vectors. Single vectors containing both the CRISPR endonuclease and the gRNAs are commercially available, thereby acting as an all-in-one vector. The method of the invention can alternatively be implemented by using two or three vectors containing the CRISPR endonuclease and the at least two gRNAs. It is also possible to use gRNA-only vectors and use cells in which the CRISPR endonuclease has been integrated into the genome. The use of an all-in-one vector that expresses the at least two gRNA and the CRISPR endonuclease is preferred since only one vector is to be introduced into the cells. A vector which can express the CRISPR endonuclease and up to seven gRNAs is, for example, described in Sakuma et al, Sci Rep. 2014; 4: 5400.

Many single gRNA empty vectors (with and without the CRISPR endonuclease) are available in the art. Likewise several empty multiplex gRNA vectors are available that can be used to express multiple gRNAs from a single plasmid (with or without the expression of the CRISPR endonuclease). Finally, also vectors are available that only express the CRISPR endonuclease (see World Wide Web Uniform Resource Locator addgene.org/crispr/empty-grna-vectors/).

The term "expressible form" requires that the one or more vectors harbour the nucleic acid molecule encoding the serine protease and the inhibitor thereof to be produced in a form that is transcribed into mRNA and translated into protein in the host cell. In this respect it is to be understood that the serine protease and the inhibitor of the serine protease are expressed, so that the inhibitor of the serine protease is present in the host cell at the same time and at the same cellular compartment as the serine protease. This may be achieved, for example, by co-expressing the serine protease and the inhibitor thereof in the host cell and/or by first initiating the expression of the inhibitor of the serine protease, so that it is already present in the host cell when the expression of the serine protease begins.

Methods for the isolation of the produced serine protease are well-known in the art and comprise without limitation method steps such as ion exchange chromatography, gel filtration chromatography (size exclusion chromatography), affinity chromatography, high pressure liquid chromatography (HPLC), reversed phase HPLC, disc gel electrophoresis or immunoprecipitation, see, for example, Sambrook et al., (2012), Molecular cloning: a laboratory manual, 4th ed., Cold Spring Harbor Laboratory Press, New York.

As is demonstrated in the examples herein below, it was surprisingly and advantageously found that the yields of a serine protease to be recombinantly produced can be significantly increased when the serine protease is expressed along with a proteinaceous inhibitor of the serine protease. This finding is illustrated on the basis of the expression of the serine protease debrilase and a total of eleven different heterologous serine protease inhibitors. Debrilase was produced in satisfactory yields with all eleven tested inhibitors. An advantageous effect on debrilase production was demonstrated for I16.001, I20.001, I11.001, I07.001, I05.001, I02.026, I02.013. The best effect on debrilase production was obtained with aprotinin. Hence, it has been unexpectedly found that the inhibitor of the serine protease can be evolutionary distinct from the serine protease but nevertheless significantly increases the production yield of the serine protease. For instance, debrilase originates from the larvae of *Lucilia sericata* whereas aprotinin originates from the pancreas of *Bos taurus* and it has been unexpectedly found that aprotinin nevertheless very significantly increases the production yield of debrilase. Aprotinin is a trypsin inhibitor whereas a natural inhibitor of debrilase has not yet been identified.

In accordance with a preferred embodiment of the first aspect of the invention, the serine protease is isolated by size-exclusion chromatography, ion-exchange chromatography, affinity chromatography, or hydrophobic interaction chromatography.

Among these isolation techniques size-exclusion chromatography and ion-exchange chromatography are preferred.

Chromatography in general is a technique for the separation of a mixture. The mixture is generally dissolved in a fluid called the mobile phase, which carries it through a structure holding another material called the stationary phase. The various constituents of the mixture travel at different speeds, causing them to separate. The separation is based on differential partitioning between the mobile and stationary phases. Size-exclusion chromatography (or molecular sieve chromatography), is a chromatographic method in which molecules in solution are separated by their size, and in some cases molecular weight. Ion-exchange chromatography (or ion chromatography) is a chromatography process that separates ions and polar molecules based on their affinity to the ion exchanger. Affinity chromatography is a method of separating biochemical mixtures based on a highly specific interaction such as that between antigen and antibody, receptor and ligand, enzyme and substrate, or enzyme and inhibitor. Finally, hydrophobic interaction chromatography is a separation technique that uses the properties of hydrophobicity to separate proteins from one another. In this type of chromatography, hydrophobic groups such as phenyl, octyl, or butyl, are attached to the stationary column. Proteins that pass through the column that have hydrophobic amino acid side chains on their surfaces are able to interact with and bind to the hydrophobic groups on the column.

In accordance with a further preferred embodiment of the first aspect of the invention, the method further comprises proteolytically processing the isolated or purified serine protease, wherein proteolytically processing preferably comprises the release of a propeptide from the serine protease by proteolytic cleavage.

As discussed herein above, serine proteases are generally initially produced in the host cell in the form of a pre-proprotein as the primary translation product. The prepeptide is cleaved-off in the endoplasmatic reticulum of the host cell. By this cleavage the pre-proprotein is transformed into the proprotein of the serine protease. The proprotein is substantially enzymatically inactive and is the major form in which the serine protease is produced in accordance with the method of the first aspect of the invention.

In accordance with the above preferred embodiment of the first aspect of the invention the proprotein may be enzymatically processed into the mature protein (i.e. the enzymatically active protein) by cleaving off the propeptide from the proprotein. The propeptide may be cleaved off the serine protease by different means e.g. when brought in contact with the enzymes being comprised in wound exudates.

In a second aspect the present invention relates to a host cell (i) comprising one or more vectors, wherein the one or more vectors encode in expressible form a serine protease and a proteinaceous inhibitor of the serine protease, or (ii) the genome of which encodes in expressible form a serine protease and a proteinaceous inhibitor of the serine protease, wherein the coding sequences of the serine protease and/or the proteinaceous inhibitor have been introduced into the host cell genome by applying a CRISPR technology, wherein the proteinaceous inhibitor of the serine protease is heterologous with respect to the serine protease.

The preferred embodiments, definitions and explanations described herein above in connection with the first aspect of the invention as far as being applicable to the second aspect of the invention apply mutatis mutandis.

In accordance with a preferred embodiment of the first and second aspect of the invention, the proteinaceous inhibitor of the serine protease is selected from the inhibitors as listed in class I02 according to the MEROPS database.

The MEROPS database is an information resource for peptidases (also termed proteases, proteinases and proteolytic enzymes) and the proteins that inhibit them. The summary page describing a given peptidase can be reached by use of an index under its name, MEROPS Identifier or source organism. The summary describes the classification and nomenclature of the peptidase and offers links to supplementary pages showing sequence identifiers, the structure if known, literature references and more.

The class (or inhibitor family) I02 according to the MEROPS database contains inhibitors of serine and cysteine peptidases. According to release 11.0 of the MEROPS database the class (or inhibitor family) I02 has the members as listed in the following Table 1.

TABLE 1

| serine protease inhibitor | MEROPS ID |
|---|---|
| aprotinin | I02.001 |
| spleen trypsin inhibitor I (*Bos taurus*) | I02.002 |
| colostrum trypsin inhibitor (*Bos taurus*) | I02.003 |
| serum basic peptidase inhibitor (*Bos taurus*) | I02.004 |
| bikunin inhibitor unit 1 | I02.005 |
| bikunin inhibitor unit 2 | I02.006 |
| hepatocyte growth factor activator inhibitor 1 inhibitor | I02.007 |

TABLE 1-continued

| serine protease inhibitor | MEROPS ID |
|---|---|
| unit 1 | |
| hepatocyte growth factor activator inhibitor 1 inhibitor unit 2 | I02.008 |
| hepatocyte growth factor activator inhibitor 2 inhibitor unit 1 | I02.009 |
| hepatocyte growth factor activator inhibitor 2 inhibitor unit 2 | I02.010 |
| tissue factor pathway inhibitor-1 inhibitor unit 1 | I02.011 |
| tissue factor pathway inhibitor-1 inhibitor unit 2 | I02.012 |
| tissue factor pathway inhibitor-2 inhibitor unit 1 | I02.013 |
| tissue factor pathway inhibitor-2 inhibitor unit 2 | I02.014 |
| protease nexin-2 | I02.015 |
| amyloid precursor-like protein 2 | I02.016 |
| peptidase inhibitor (*Tachypleus*) | I02.017 |
| chymotrypsin inhibitor SCI-I (*Bombyx mori*) | I02.018 |
| paragonial peptide D (*Drosophila funebris*) | I02.019 |
| boophilin inhibitor unit 1 | I02.020 |
| boophilin inhibitor unit 2 | I02.021 |
| chelonianin inhibitor unit 1 | I02.022 |
| carrapatin | I02.023 |
| ornithodorin inhibitor unit 1 | I02.024 |
| ixolaris (*Ixodes scapularis*) | I02.025 |
| peptidase inhibitor 5 (*Anemonia sulcata*) | I02.026 |
| fraction IX inhibitor (*Bungarus fasciatus*) | I02.031 |
| ornithodorin inhibitor unit 2 | I02.032 |
| WFIKKN peptidase inhibitor inhibitor unit 3 | I02.033 |
| Ac-KPI-1 I (*Ancylostoma caninum*) inhibitor unit 5, 6, or 8 | I02.034 |
| savignin (*Ornithodoros savignyi*) | I02.035 |
| FhKT1 (*Fasciola hepatica*) | I02.036 |
| Kil-1 protein (*Drosophila virilis*) | I02.037 |
| penthalaris (*Ixodes scapularis*) | I02.038 |
| amblin inhibitor unit 1 (*Amblyomma hebraeum*) | I02.039 |
| HiTI serine peptidase inhibitor (*Haematobia irritans*) | I02.040 |
| haemaphysalin unit 1 | I02.050 |
| haemaphysalin unit 2 | I02.051 |
| textilinin-1 (*Pseudonaja textilis*) | I02.052 |
| TdPI tryptase inhibitor (*Rhipicephalus appendiculatus*) | I02.053 |
| BmTI-6 (*Boophilus microplus*) | I02.054 |
| OH-TCI trypsin/chymotrypsin inhibitor (*Ophiophagus hannah*) | I02.055 |
| HWTI trypsin inhibitor (*Ornithoctonus huwena*) | I02.056 |
| hemalin (*Haemaphysalis longicornis*) | I02.057 |
| eppin-3, inhibitor unit 2 | I02.058 |
| BmCI chymotrypsin inhibitor (*Rhipicephalus microplus*) | I02.059 |
| DvKPI (*Dermacentor variabilis*) | I02.060 |
| Kunitz inhibitor (*Heteractis crispa*-type) | I02.061 |
| plasma kallikrein inhibitor (*Oxyuranus* sp.) | I02.062 |
| tryptogalanin (*Ixodes scapularis*) | I02.063 |
| SmCI inhibitor unit 1 (*Sabellastarte magnifica*) | I02.064 |
| tissue factor pathway inhibitor-1 unit 3 | I02.950 |
| tissue factor pathway inhibitor-2 unit 3 | I02.951 |
| amblin inhibitor unit 2 (*Amblyomma hebraeum*) | I02.952 |
| WFIKKN peptidase inhibitor inhibitor unit 2 | I02.953 |
| WFIKKNRP putative peptidase inhibitor unit 2 | I02.954 |
| WFIKKNRP putative peptidase inhibitor unit 3 | I02.955 |
| eppin inhibitor unit 2 | I02.956 |
| Ac-KPI-1 I (*Ancylostoma caninum*) inhibitor unit 1 | I02.957 |
| Ac-KPI-1 I (*Ancylostoma caninum*) inhibitor unit 2 | I02.958 |
| Ac-KPI-1 I (*Ancylostoma caninum*) inhibitor unit 3 | I02.959 |
| Ac-KPI-1 I (*Ancylostoma caninum*) inhibitor unit 4 | I02.960 |
| Ac-KPI-1 I (*Ancylostoma caninum*) inhibitor unit 7 | I02.961 |
| Ac-KPI-1 I (*Ancylostoma caninum*) inhibitor unit 9 | I02.962 |
| Ac-KPI-1 I (*Ancylostoma caninum*) inhibitor unit 10 | I02.963 |
| Ac-KPI-1 I (*Ancylostoma caninum*) inhibitor unit 11 | I02.964 |
| Ac-KPI-1 I (*Ancylostoma caninum*) inhibitor unit 12 | I02.965 |
| collagen alpha 1(VII) chain | I02.967 |
| collagen alpha 3(VI) chain | I02.968 |
| HKIB9 | I02.969 |
| WFDC8 protein (*Homo sapiens*) | I02.971 |
| papilin | I02.972 |
| LOC131875 protein (*Homo sapiens*) and similar | I02.973 |
| LOC222978 protein (*Homo sapiens*) and similar | I02.974 |
| 9230105I15Rik protein (*Mus musculus*) and similar | I02.975 |
| LOC209351 protein unit 2 (*Mus musculus*) and similar | I02.976 |
| LOC228863 protein (*Mus musculus*) and similar | I02.977 |
| LOC277343 protein (*Mus musculus*) and similar | I02.978 |

Accordingly, the proteinaceous inhibitor of the serine protease is more preferably selected from the inhibitors as listed in the above Table 1. In the examples herein below five members of the class (or inhibitor family) I02 according to the MEROPS database were tested. Debrilase could be produced in satisfactory yields with all five members.

In accordance with another preferred embodiment of the first and second aspect of the invention, the proteinaceous inhibitor is selected from the group consisting of aprotinin, plasminostreptin (I16.001), proteinase inhibitor type-2 K (PIN2K, I20.001), ecotin (I11.001), trypsin inhibitor MCTI-1 (I07.001), ascidian trypsin inhibitor (I05.001), peptidase inhibitor 5 (KappaPI-actitoxin-Avd3a, I02.026), and tissue factor pathway inhibitor-2 inhibitor unit 1 (TFPI2, I02.013). The examples herein below show that debrilase was produced in good yields with all five members.

In accordance with a more preferred embodiment of the first and second aspect of the invention, the proteinaceous inhibitor of the serine protease is aprotinin. As shown in the examples herein below the best effect on debrilase production was obtained with aprotinin.

Aprotinin (or bovine pancreatic trypsin inhibitor (BPTI)) is the founding member of the class (or inhibitor family) I02 according to the MEROPS database and is used in the examples herein below as the inhibitor of the serine protease of debrilase. Aprotinin has the amino acid sequence of SEQ ID NO: 1 which amino acid sequence is encoded by the nucleotide sequence of SEQ ID NO: 2. As mentioned above, aprotinin is a bovine pancreatic trypsin inhibitor. Aprotinin is a competitive serine protease inhibitor which forms stable complexes with and blocks the active sites of enzymes. The binding is reversible, and most aprotinin-protease complexes dissociate at pH >10 or <3.2. SEQ ID NO: 2 is a nucleotide sequence being codon-optimized for the expression in *Pichia pastoris* cells. Codon optimization is widely used for designing synthetic genes to improve their expression in a heterologous host organism. Because not all tRNAs are expressed equally or at the same level across organisms, a particular nucleotide sequence can be codon-optimized by changing its codons to match the most prevalent tRNA in a particular heterologous host organism. A codon-optimized nucleotide sequence is generally more efficiently translated as compared to the non codon-optimized nucleotide sequence.

In accordance with a further preferred embodiment of the first and second aspect of the invention, the serine protease is a serine protease having the EC number 3.4.21.

Serine proteases are classified in the BRENDA database as having the EC number 3.4.21. The Enzyme Commission number (EC number) is a numerical classification scheme for enzymes, based on the chemical reactions they catalyze. The enzyme nomenclature scheme was developed starting in 1955, when the International Congress of Biochemistry in Brussels set up an Enzyme Commission. The first version was published in 1961. The BRENDA database is an information system representing one of the most comprehensive enzyme repositories. BRENDA was founded in 1987 at the former German National Research Centre for Biotechnology. It was originally published as a series of books but is now an online database that comprises molecular and biochemical information on enzymes. The serine protease debrilase and the serine proteases having the EC number 3.4.21 comprised in the BRENDA database release 2017.1 are listed in Table 2.

TABLE 2

| serine protease | EC number |
| --- | --- |
| debrilase | 3.4.21 |
| chymotrypsin | +.4.21.1 |
| chymotrypsin C | 3.4.21.2 |
| metridin | 3.4.21.3 |
| trypsin | 3.4.21.4 |
| thrombin | 3.4.21.5 |
| coagulation factor Xa | 3.4.21.6 |
| plasmin | 3.4.21.7 |
| kallikrein | 3.4.21.8 |
| enteropeptidase | 3.4.21.9 |
| acrosin | 3.4.21.10 |
| elastase | 3.4.21.11 |
| alpha-lytic endopeptidase | 3.4.21.12 |
| phaseolus proteinase | 3.4.21.13 |
| microbial serine proteases | 3.4.21.14 |
| Aspergillus alkaline proteinase | 3.4.21.15 |
| Alternaria serine proteinase | 3.4.21.16 |
| Arthrobacter serine proteinase | 3.4.21.17 |
| Tenebrio alpha-proteinase | 3.4.21.18 |
| glutamyl endopeptidase | 3.4.21.19 |
| cathepsin G | 3.4.21.20 |
| coagulation factor VIIa | 3.4.21.21 |
| coagulation factor IXa | 3.4.21.22 |
| Vipera russelli proteinase | 3.4.21.23 |
| red cell neutral endopeptidase | 3.4.21.24 |
| cucumisin | 3.4.21.25 |
| prolyl oligopeptidase | 3.4.21.26 |
| coagulation factor XIa | 3.4.21.27 |
| Agkistrodon serine proteinase | 3.4.21.28 |
| Bothrops atrox serine proteinase | 3.4.21.29 |
| Crotalus adamanteus serine proteinase | 3.4.21.30 |
| urokinase | 3.4.21.31 |
| brachyurin | 3.4.21.32 |
| Entomophthora collagenolytic proteinase | 3.4.21.33 |
| plasma kallikrein | 3.4.21.34 |
| tissue kallikrein | 3.4.21.35 |
| pancreatic elastase | 3.4.21.36 |
| leukocyte elastase | 3.4.21.37 |
| coagulation factor XIIa | 3.4.21.38 |
| chymase | 3.4.21.39 |
| submandibular proteinase A | 3.4.21.40 |
| complement subcomponent C1r | 3.4.21.41 |
| complement subcomponent C1s | 3.4.21.42 |
| classical-complement-pathway C3/C5 convertase | 3.4.21.43 |
| complement component C5 convertase | 3.4.21.44 |
| complement factor I | 3.4.21.45 |
| complement factor D | 3.4.21.46 |
| alternative-complement-pathway C3/C5 convertase | 3.4.21.47 |
| cerevisin | 3.4.21.48 |
| hypodermin C | 3.4.21.49 |
| lysyl endopeptidase | 3.4.21.50 |
| leukocyte-membrane neutral endopeptidase | 3.4.21.51 |
| cathepsin R | 3.4.21.52 |
| Endopeptidase La | 3.4.21.53 |
| gamma-Renin | 3.4.21.54 |
| Venombin AB | 3.4.21.55 |
| euphorbain | 3.4.21.56 |
| Leucyl endopeptidase | 3.4.21.57 |
| prohormone serine proteinase | 3.4.21.58 |
| Tryptase | 3.4.21.59 |
| Scutelarin | 3.4.21.60 |
| Kexin | 3.4.21.61 |
| Subtilisin | 3.4.21.62 |
| Oryzin | 3.4.21.63 |
| peptidase K | 3.4.21.64 |
| Thermomycolin | 3.4.21.65 |
| Thermitase | 3.4.21.66 |
| Endopeptidase So | 3.4.21.67 |
| t-Plasminogen activator | 3.4.21.68 |
| Protein C (activated) | 3.4.21.69 |
| Pancreatic endopeptidase E | 3.4.21.70 |
| Pancreatic elastase II | 3.4.21.71 |
| IgA-specific serine endopeptidase | 3.4.21.72 |
| u-Plasminogen activator | 3.4.21.73 |
| venombin A | 3.4.21.74 |
| Furin | 3.4.21.75 |
| Myeloblastin | 3.4.21.76 |
| semenogelase | 3.4.21.77 |

TABLE 2-continued

| serine protease | EC number |
| --- | --- |
| Granzyme A | 3.4.21.78 |
| Granzyme B | 3.4.21.79 |
| Streptogrisin A | 3.4.21.80 |
| Streptogrisin B | 3.4.21.81 |
| Glutamyl endopeptidase II | 3.4.21.82 |
| Oligopeptidase B | 3.4.21.83 |
| limulus clotting factor C | 3.4.21.84 |
| limulus clotting factor B | 3.4.21.85 |
| limulus clotting enzyme | 3.4.21.86 |
| omptin | 3.4.21.87 |
| Repressor LexA | 3.4.21.88 |
| Signal peptidase I | 3.4.21.89 |
| Togavirin | 3.4.21.90 |
| Flavivirin | 3.4.21.91 |
| Endopeptidase Clp | 3.4.21.92 |
| Proprotein convertase 1 | 3.4.21.93 |
| proprotein convertase 2 | 3.4.21.94 |
| Snake venom factor V activator | 3.4.21.95 |
| Lactocepin | 3.4.21.96 |
| assemblin | 3.4.21.97 |
| hepacivirin | 3.4.21.98 |
| spermosin | 3.4.21.99 |
| sedolisin | 3.4.21.100 |
| xanthomonalisin | 3.4.21.101 |
| C-terminal processing peptidase | 3.4.21.102 |
| physarolisin | 3.4.21.103 |
| mannan-binding lectin-associated serine protease-2 | 3.4.21.104 |
| rhomboid protease | 3.4.21.105 |
| hepsin | 3.4.21.106 |
| peptidase Do | 3.4.21.107 |
| HtrA2 peptidase | 3.4.21.108 |
| matriptase | 3.4.21.109 |
| C5a peptidase | 3.4.21.110 |
| aqualysin 1 | 3.4.21.111 |
| site-1 protease | 3.4.21.112 |
| pestivirus NS3 polyprotein peptidase | 3.4.21.113 |
| equine arterivirus serine peptidase | 3.4.21.114 |
| infectious pancreatic necrosis birnavirus Vp4 peptidase | 3.4.21.115 |
| SpoIVB peptidase | 3.4.21.116 |
| stratum corneum chymotryptic enzyme | 3.4.21.117 |
| kallikrein 8 | 3.4.21.118 |
| kallikrein 13 | 3.4.21.119 |
| oviductin | 3.4.21.120 |
| Lys-Lys/Arg-Xaa endopeptidase | 3.4.21.121 |
| hyaluronan-binding serine protease | 3.4.21.B1 |
| granzyme M | 3.4.21.B2 |
| duodenase | 3.4.21.B3 |
| granzyme K | 3.4.21.B4 |
| mast cell protease 5 | 3.4.21.B5 |
| prostasin | 3.4.21.B6 |
| mannan-binding lectin-associated serine protease 1 | 3.4.21.B7 |
| neurosin | 3.4.21.B10 |
| prostase | 3.4.21.B12 |
| trepolisin | 3.4.21.B21 |
| proprotein convertase 4 | 3.4.21.B24 |
| PACE4 proprotein convertase | 3.4.21.B25 |
| proprotein convertase 5 | 3.4.21.B26 |
| proprotein convertase 7 | 3.4.21.B27 |
| fibroblast activation protein alpha subunit | 3.4.21.B28 |
| UmuD protein | 3.4.21.B30 |
| tricorn core protease (archaea) | 3.4.21.B34 |
| stratum corneum tryptic enzyme | 3.4.21.B39 |
| kallikrein 9 | 3.4.21.B40 |
| kallikrein 10 | 3.4.21.B41 |
| hippostasin | 3.4.21.B42 |
| kallikrein 12 | 3.4.21.B43 |
| kallikrein 14 | 3.4.21.B45 |
| kumamolysin | 3.4.21.B48 |
| ctpB peptidase | 3.4.21.B49 |
| DegQ peptidase | 3.4.21.B50 |
| thermostable serine endopeptidase (Sulfolobus) | 3.4.21.B52 |
| Pyrococcus abyssi serine endopeptidase | 3.4.21.B54 |
| pyrolysin | 3.4.21.B55 |
| *Pyrococcus horikoshii* membrane protease PH1510 | 3.4.21.B56 |
| pernisine | 3.4.21.B57 |
| pernilase | 3.4.21.B58 |
| granzyme H | 3.4.21.B59 |

Accordingly, the serine protease is more preferably selected from the enzymes as listed in the above Table 2.

In accordance with a more preferred embodiment of the first and second aspect of the invention, the serine protease is debrilase.

Debrilase (or Aurase®) was identified by molecular cloning and originates from the larvae of *Lucilia sericata* (WO 2010/099955). The amino acid sequence of the pre-proprotein of debrilase is shown in SEQ ID NO: 3, of the proprotein of debrilase in SEQ ID NO: 4, and of the mature debrilase protein in SEQ ID NO: 5. The nucleotide sequence of SEQ ID NO: 6 encodes the amino acid sequence of SEQ ID NO: 3. SEQ ID NO: 4 is encoded by SEQ ID NO: 7 and SEQ ID NO: 5 by SEQ ID NO: 8. Mature debrilase has the ability to cleave fibrin and casein. The name debrilase reflects that the enzyme is useful for debridement of wounds.

Debridement is defined as the removal of non-vital tissue from wounds. In chronic wounds, debridement means the elimination of necrosis as well as the clearing away of wound dressings, foreign bodies, and other non-vital substances. In addition to treating the causal factors for delayed wound healing, debridement should be the first step in an adequate treatment of chronic wounds. Different methods for debridement in chronic wounds have been described such as surgery, maggot therapy, laser, ultrasound, hydrotherapy, wet-to-dry method, autolysis, osmotic or chemical debridement, and the use of proteolytic enzymes.

An expression system for debrilase was developed in *Escherichia coli* BL21 as a prokaryotic host and *Pichia pastoris* as a eukaryotic host (WO 2010/99955).

In accordance with a further preferred embodiment of the first and second aspect of the invention, the host cell is (a) a yeast cell, preferably a *Pichia pastoris* cell; (b) a bacterial cell, preferably a *Escherichia coli* or a *Bacillus subtilis* cell, or (c) a filamentous fungal cell, preferably an *Aspergillus* spec. cell.

Yeast cells, filamentous fungal cells and bacterial cells are frequently used in the art as host cells in order to recombinantly produce proteins. In particular for these host cells the molecular biology of the expression vectors as well as the choice of promoters, tags and codon optimizations of the target genes are well determined, so that a high-yielding protein production can be achieved.

The host cell is more preferably a yeast cell, and most preferably a *Pichia pastoris* cell, noting that *Pichia pastoris* cells are used as host cells in the examples herein below.

In accordance with a yet further preferred embodiment of the first and second aspect of the invention, the serine protease is not a natural substrate of the serine protease inhibitor.

As discussed above, in the examples the serine protease debrilase from of *Lucilia sericata* has been produced along with the serine protease inhibitor aprotinin from *Bos taurus*. Although the natural substrate of aprotinin is bovine trypsin it has been surprisingly found that aprotinin is effective in inhibiting the non-natural substrate and evolutionary distinct serine protease debrilase. Advantageously, the production of debrilase along with aprotinin significantly enhances the production yields of the recombinant debrilase. In this respect is also of note that an inhibitor having debrilase as its natural substrate is not known to the best knowledge of the inventors.

In accordance with another preferred embodiment of the first and second aspect of the invention, the serine protease and the proteinaceous serine protease inhibitor are co-expressed in the host-cell.

In this connection the term "co-expressed" requires that the serine protease and proteinaceous serine protease inhibitor are expressed at the same time in the host. This may be achieved by several ways. Co-expression may, for example, be achieved by placing the genes encoding the serine protease and proteinaceous serine protease inhibitor under the control of the same transcriptional regulatory program, functionally related regulatory programs, or transcriptional regulatory members of the same pathway or protein complex.

In accordance with a preferred embodiment of the first and second aspect of the invention, in the one or more vectors the serine protease is expressed from a first expression cassette and the proteinaceous inhibitor of the serine protease is expressed from a second expression cassette, wherein the first and second expression cassettes are preferably on two separate vectors.

In accordance with this preferred embodiment the serine protease and the proteinaceous inhibitor are expressed from different expression cassettes. This ensures that in the host cell the serine protease and the proteinaceous inhibitor are produced by translation from two separate mRNA species. This also allows for placing the expression of the serine protease and the proteinaceous inhibitor under the control of the same or different promoters. In this respect is of note that several promoters are available in the art and the promotors in the first and second expression cassette may be selected in order to control, for example, the amounts, location and/or timing of the expression—separately for each expression cassette or for both expression cassettes in the same manner. The at least two expression cassettes may be present in one vector and are preferably present in at least two vectors, so that the serine protease and the proteinaceous inhibitor are expressed from two different vectors. In this respect it is preferred that the timing when high levels of the proteinaceous inhibitor are produced is coordinated with the expression of the serine protease, so that high levels of the proteinaceous inhibitor and high levels of the serine protease are present at the same time in the host cell.

In accordance with a more preferred embodiment of the first and second aspect of the invention, the serine protease and the proteinaceous inhibitor of the serine protease are under the control of the same or different strong, regulated promoter(s).

In accordance with a further more preferred embodiment of the first and second aspect of the invention, the serine protease is under the control of the same strong, regulated promoter as the proteinaceous inhibitor of the serine protease In the examples debrilase and aprotinin were expressed from two expression cassettes in two vectors, wherein debrilase and aprotinin were expressed under the control of the same strong, regulated promoter. It has been found that outstandingly high levels of the serine protease debrilase can be produced in case this mode of expression is used without toxic effects for the host cell.

In accordance with an even more preferred embodiment of the first and second aspect of the invention, the host cell is a *Pichia pastoris* cell and/or the strong, regulated promoter is $P_{aox}$ (alcohol oxidase promoter), preferably is $P_{aox1}$ or $P_{aox2}$.

*Pichia pastoris* is widely used for protein production using recombinant DNA techniques. *Pichia pastoris* has two alcohol oxidase genes, Aox1 and Aox2, which have a strongly inducible promoter. These genes allow *Pichia pas-* toris to use methanol as a carbon and energy source. The AOX promoters are induced by methanol and are repressed by e.g. glucose.

In the examples herein below *Pichia pastoris* cells were used as the host cells, debrilase as well as aprotinin were expressed under the control of the strong, regulated promoter $P_{aox}$ (alcohol oxidase promoter).

Regarding the embodiments characterized in this specification, in particular in the claims, it is intended that each embodiment mentioned in a dependent claim is combined with each embodiment of each claim (independent or dependent) said dependent claim depends from. For example, in case of an independent claim 1 reciting 3 alternatives A, B and C, a dependent claim 2 reciting 3 alternatives D, E and F and a claim 3 depending from claims 1 and 2 and reciting 3 alternatives G, H and I, it is to be understood that the specification unambiguously discloses embodiments corresponding to combinations A, D, G; A, D, H; A, D, I; A, E, G; A, E, H; A, E, I; A, F, G; A, F, H; A, F, I; B, D, G; B, D, H; B, D, I; B, E, G; B, E, H; B, E, I; B, F, G; B, F, H; B, F, I; C, D, G; C, D, H; C, D, I; C, E, G; C, E, H; C, E, I; C, F, G; C, F, H; C, F, I, unless specifically mentioned otherwise.

Similarly, and also in those cases where independent and/or dependent claims do not recite alternatives, it is understood that if dependent claims refer back to a majority of preceding claims, any combination of subject-matter covered thereby is considered to be explicitly disclosed. For example, in case of an independent claim 1, a dependent claim 2 referring back to claim 1, and a dependent claim 3 referring back to both claims 2 and 1, it follows that the combination of the subject-matter of claims 3 and 1 is clearly and unambiguously disclosed as is the combination of the subject-matter of claims 3, 2 and 1. In case a further dependent claim 4 is present which refers to any one of claims 1 to 3, it follows that the combination of the subject-matter of claims 4 and 1, of claims 4, 2 and 1, of claims 4, 3 and 1, as well as of claims 4, 3, 2 and 1 is clearly and unambiguously disclosed.

The above considerations apply mutatis mutandis to all appended claims.

The figures show:

FIG. 1

Half maximal inhibitory concentration (IC50) of aprotinin inhibition of debrilase activity. The activity of debrilase was determined using the fluorescence labelled substrate peptide Z-Gly-Gly-Arg-AMC in PBS buffer (pH 8). The debrilase activity without adding aprotinin was defined as 100% activity.

FIG. 2

Plasmid map of expression vector for co-expression of debrilase and aprotinin. Scheme of the constructed plasmid pPpT4_$P_{AOX}$_Apr_Pp, kanamycin$^r$ that was used for the construction of *P. pastoris* AurPlus. The modified aprotinin encoding gene (SEQ ID NO: 3) was cloned under control of the strong inducible promoter Paox.

FIG. 3

Analysis of debrilase and aprotinin produced by *P. pastoris* AurPlus in shake flask scale. Production of prodebrilase and aprotinin was visualized on SDS-PAGE. Arrows indicate both molecules. M: Benchmark Protein Ladder (kDa), 1: t=0 min after induction, 2: t=24 h after induction, 3: t=48 h after induction, 4: t=72 h after induction.

FIG. 4

Analysis of *P. pastoris* AurPlus Secretion Product a) Possible secreted products of *P. pastoris*. Numbers illustrate the molecular weight. b) Debrilase PK are samples of activated debrilase. These samples were analyzed against supernatant samples from the novel expression strain showing that debrilase is secreted as prodebrilase (higher molecular weight). The SDS-PAGE was run in order to analyse only the debrilase molecules. Aprotinin was not monitored due to long run time of the SDS-PAGE.

FIG. 5

Activation of prodebrilase. Prodebrilase from the supernatant of *P. pastoris* AurPlus was incubated at pH 8 for 0-60 minutes. Before incubation, the pH of the debrilase solution was shifted from pH 5 to pH 8. The activation (size shift) takes place after 10 minutes of incubation. M: benchmark protein ladder (kDa), start: pH shift from pH5 to pH8.

FIG. 6

Quantification of debrilase production

Densitometric analysis of *P. pastoris* AurPlus supernatant and reference debrilase for quantification of prodebrilase production level. M: benchmark protein ladder (kDa), 1-5: dilution series (1:2) of *P. pastoris* AurPlus supernatant, 6-10: dilution series (1:2) of reference debrilase with known concentration.

FIG. 7

Analysis of debrilase and different inhibitors produced by *P. pastoris*. Production of debrilase and different inhibitors from different inhibitor classes was visualized on SDS-PAGE. M: benchmark protein ladder (kDa), 1: Ref1—*P. pastoris* AurPlus 2: Ref2—*P. pastoris* (U.S. Pat. No. 8,623,810 B2), 3-9: Coexpression strains, expressed inhibitor according to MEROPS ID. Molecular weight of the inhibitors: I16_001 (11.4 kDa), I20_001 (13.8 kDa), I11_001 (16.1 kDa), I07_001 (3.4 kDa), I05_001 (6.1 kDa), I02_026 (6.9 kDa), I02_013 (7.4 kDa). The Examples illustrate the invention.

EXAMPLE 1: IDENTIFICATION AND CHARACTERIZATION OF APROTININ AS SUITABLE DEBRILASE INHIBITOR

Proteinaceous protease inhibitors that are capable of inhibiting trypsin-like serine proteases were selected by literature search (Protein Databank). The protease inhibitor aprotinin from bovine lung (Sigma Aldrich), member of the MEROPS class I02, was selected and tested for its potential activity on inhibiting the proteolytic activity of debrilase.

Figure 1:
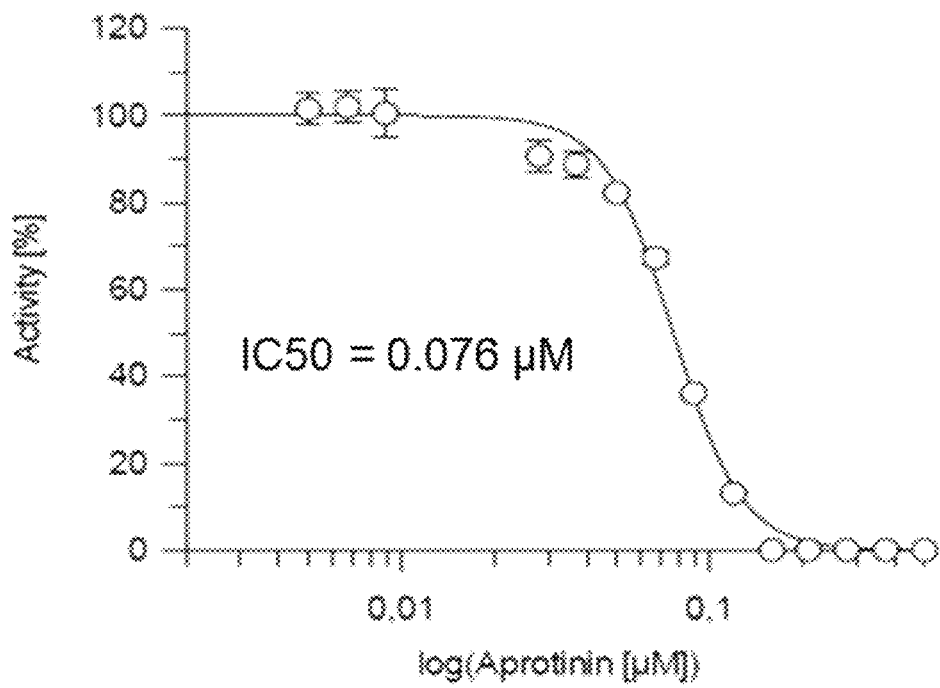

Aprotinin was added to a debrilase sample (5 mg/L debrilase) in concentrations from 0.005-0.5 μM and incubated for 0.5 h at 4° C. After incubation, the residual debrilase activity was analyzed using Z-Gly-Gly-Arg-AMC (Bachem) as substrate. The kinetic of activity was determined in PBS buffer (pH 8) at 37° C. The release of 7-amino-4-methylcoumarin (AMC) was measured with a BMC Novostar Fluorometer ($\lambda$ex 365 nm, $\lambda$em 440 nm). Surprisingly, aprotinin was identified as potent non-natural debrilase inhibitor. A half maximal inhibitory concentration (IC50) of 0.076 μM was determined (FIG. 1).

A second commercially available proteinaceous protease inhibitor that was tested was the trypsin inhibitor from *Phaseolus limensis* (lima bean). This inhibitor belonging to the Bowman-Birk class of inhibitors was not able to inhibit the debrilase activity. Therefore, the focus was first on aprotinin, and then other members of the MEROPS database were successfully tested (see example 7).

EXAMPLE 2: DESIGN OF THE APROTININ GENE SEQUENCE AND CONSTRUCTION OF A *P. PASTORIS* CO-EXPRESSION STRAIN

*Pichia pastoris* is a suitable expression host for the heterologous production of aprotinin (Vedvick Vedvick, T. et al. (1991) High-level secretion of biologically active aprotinin from the yeast Pichia pastoris. J Ind Microbiol 7, 197-201). The aprotinin amino acid sequence (SEQ ID NO: 1) was used for the design of a codon optimized gene sequence. An N-terminal extension of the bases GAAGCT was added for efficient secretion and processing in *P. pastoris* to the nucleotide sequence encoding aprotinin (SEQ ID NO: 2) as described by Zsebo et al. (1986), Protein secretion from *Saccharomyces cerevisiae* directed by the prepro-alpha-factor leader region. J Biol Chem 261:5858-5865. This fusion construct has the amino acid sequence of SEQ ID NO: 9 and the nucleotide sequence of SEQ ID NO: 10. The designed aprotinin fusion sequence was furthermore fused to the gene sequence of the alpha mating factor from *S. cerevisiae*. Said further fusion construct has the amino acid sequence of SEQ ID NO: 11 and the nucleotide sequence of SEQ ID NO: 12.

Figure 2:
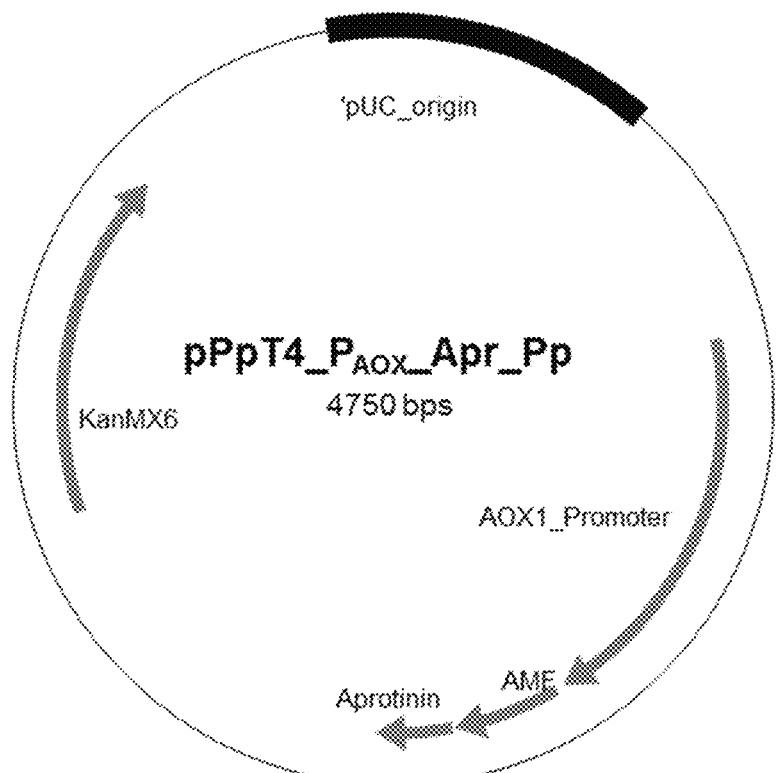

The pPpT4 expression plasmids were used as shuttle to transfer the modified aprotinin sequence into the debrilase producing *P. pastoris* (U.S. Pat. No. 8,623,810 B2), wherein the debrilase encoding expression cassette is stably integrated in the genome. For the construction of pPpT4_$P_{AOX}$_Apr_Pp (FIG. 2), the aprotinin sequence was ligated into the sites EcoRI and NotI of pPpT4 plasmid. The plasmid was used for transformation of *P. pastoris* expressing the debrilase gene under control of the AOX1 promoter (U.S. Pat. No. 8,623,810 B2). Before transformation, the plasmid was cut by SacI for pPpT4_$P_{AOX}$_Apr_Pp for plasmid linearization. Gene cloning was performed in *E. coli* using restriction endonucleases and ligase from New England Biolabs. The original debrilase expressing strain was transformed with linearized pPpT4_$P_{AOX}$_Apr_Pp for subsequent integration into the *P. pastoris* genome. For selection of positive integrands, antibiotic markers were used. The plasmid pPpT4_$P_{AOX}$_Apr_Pp carries the gene information for kanamycin6 resistance. The strains were cultured on YPD agar plates for 3 days containing Zeocin (100 µg/ml) (selection of debrilase expression cassette as described in WO2010099955) Zeocin+Geneticin (50 µg/ml) (selection of expression cassette for aprotinin under $P_{AOX}$ promoter control)

EXAMPLE 3: IDENTIFICATION OF STRONG DEBRILASE PRODUCERS

Clones that show the correct phenotype on selection agar plates were picked and cultivated in small scale for expression studies. 12 clones from each type were cultivated in 500 µl EnPresso Y medium (Biosilta) for 90 h. The standard protocol was used for feeding and induction. Clones were randomly analyzed via SDS-PAGE. For the identification of positive clones, these clones that show strong debrilase production and no proteolytic activity were determined as hit. An activity assay using the fluorescence labelled peptide Z-Gly-Gly-Arg-AMC was used for activity determination. One hit was detected from the screening. This clone shows a high potential for debrilase production, produced detectable amounts of aprotinin and showed no proteolytic activity. This improved debrilase production strain was termed *P. pastoris* AurPlus.

Figure 3:
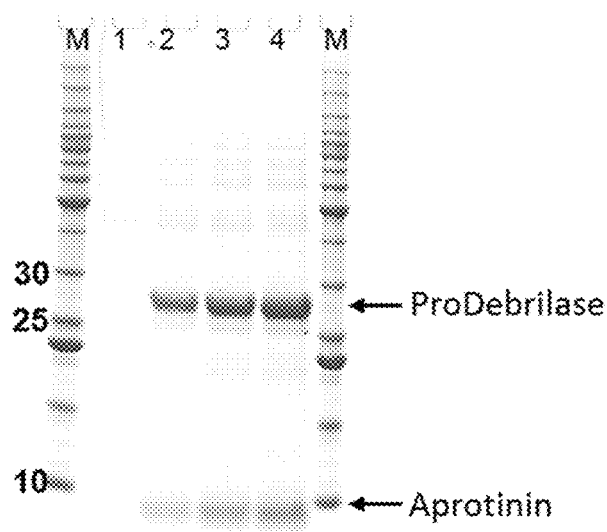

*P. pastoris* AurPlus was transferred into shake flask scale. The cultivation was done in 20 ml EnPresso Y medium for 90 h using the standard protocol for feeding and induction. The debrilase and aprotinin production capacities were analyzed by SDS-PAGE (FIG. 3). *P. pastoris* AurPlus shows strong production of debrilase as well as aprotinin.

The secreted debrilase from *P. pastoris* AurPlus was analyzed via SDS-PAGE to determine whether it is produced as mature debrilase that is inhibited by aprotinin or as prodebrilase (FIGS. 4 *a* and *b*). The secreted debrilase was compared to mature and active debrilase. The size shift that is visible between mature debrilase and the secreted debrilase (higher molecular weight) illustrates that *P. pastoris* AurPlus produces the inactive pro-form of the molecule (prodebrilase).

EXAMPLE 4: SEPARATION OF PRODEBRILASE AND APROTININ

For the separation of prodebrilase and aprotinin, several chromatography methods were used. One of these methods was ion exchange chromatography (cation exchange) that was performed at pH 5 using a 5 ml Sepharose SP column. The supernatant sample of *P. pastoris* AurPlus was diafiltrated against 7 diavolumes of citrate buffer (1.05 g/L citric acid monohydrate, 1.42 g/L sodium phosphate dibasic, 11.69 g/L NaCl) buffer. 30 ml of diafiltrated sample was run with a flow of 3 ml/min. The buffers A (citrate buffer) and buffer B (citrate buffer with 1 M NaCl) were used. The ion exchange was run with a linear gradient starting with a wash step with 10 column volumes of 100% buffer A. For elution, a linear gradient of 0-100% with buffer B over 15 column volumes was run. Fractions of 2 ml were collected and fractions 10-29 were analyzed on SDS-PAGE for protein distribution. Prodebrilase and aprotinin were separated via ion exchange chromatography. Prodebrilase elutes early in fractions 17-22. Aprotinin elutes in fractions 24-28.

EXAMPLE 5: ACTIVATION OF PRODEBRILASE

Figure 5:
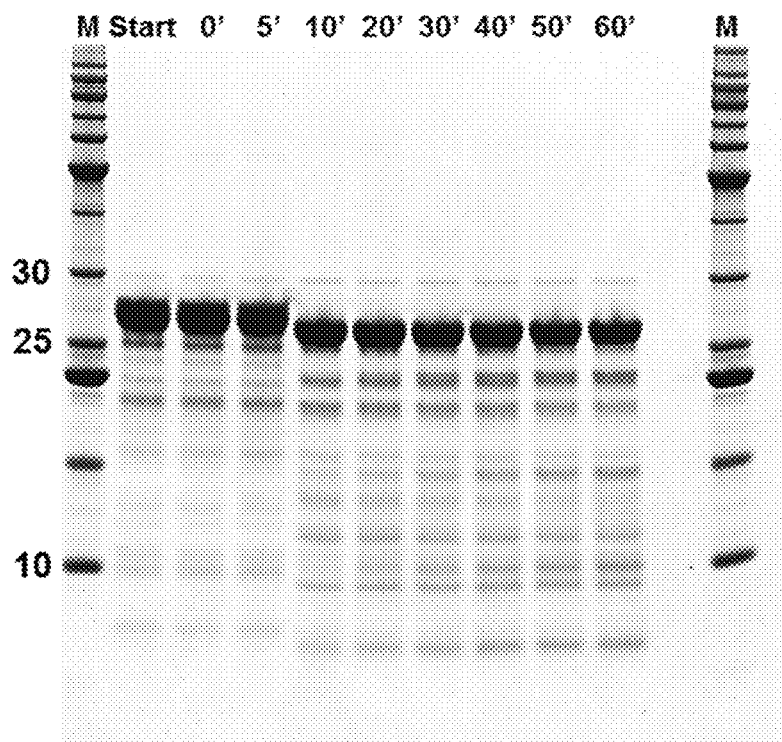

The fractions containing prodebrilase from ion exchange chromatography were pooled and used for activation experiments. The pH of the pooled sample was shifted from pH 5 after the ion exchange chromatography to pH 8. The sample was incubated for 1 h at 37° C. and pH 8 to induce autocatalytic activation (processing) of the protease. The processing of debrilase (size shift) by releasing the propeptide was analyzed by SDS-PAGE (FIG. 5).

EXAMPLE 6: QUANTIFICATION OF PRODEBRILASE PRODUCTION BY *P. PASTORIS* AURPLUS

Figure 6:
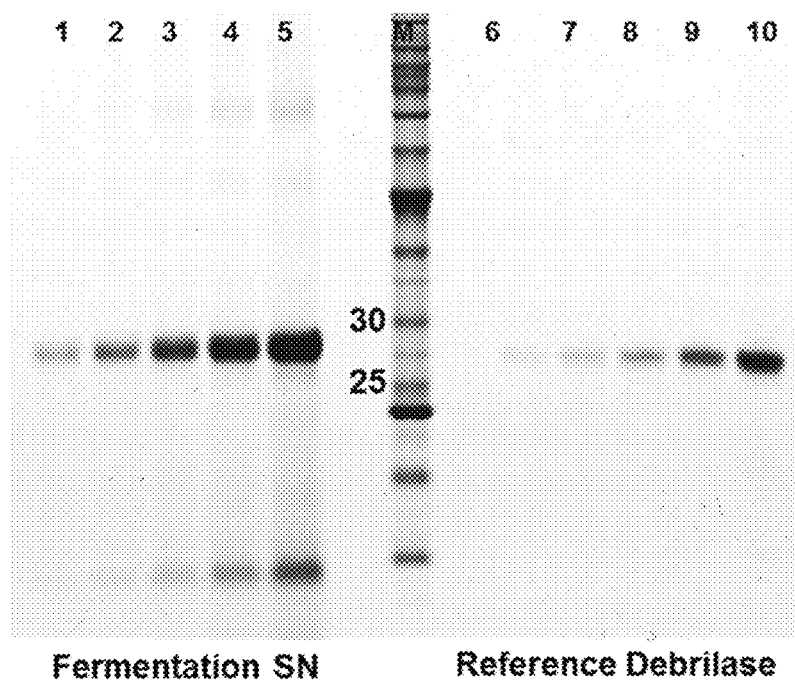

*P. pastoris* AurPlus was cultured in a 2 L fermenter. In general, the fermentation was performed using Gasser medium (high salt). The three phases of fermentation included a batch phase with 40 g/L glycerol, a first feed phase over 12 h with an exponential feed of 80 glycerol, µ=0.1 and a second exponential feed phase over 48 h with 100% methanol µ=0.03. After fermentation, the supernatant of the production strain was collected by centrifugation and used for densitometric analysis in order to determine the prodebrilase production level. The supernatant was diluted from 1:1 to 1:8 in 1:2 dilution steps and analyzed on SDS-PAGE. As reference, mature debrilase with a known concentration of 4.8 g/L was used for calculation of prodebrilase amounts (FIG. 6). Densitometric analysis revealed that *P. pastoris* AurPlus is capable of producing 1.4 g/L (+/−0.05 g/L) prodebrilase which is nearly a thirteen-fold increase compared to the original debrilase production strain.

EXAMPLE 7: IDENTIFICATION OF FURTHER SUITABLE HETEROLOGOUS PROTEINACEOUS INHIBITORS

Figure 7:
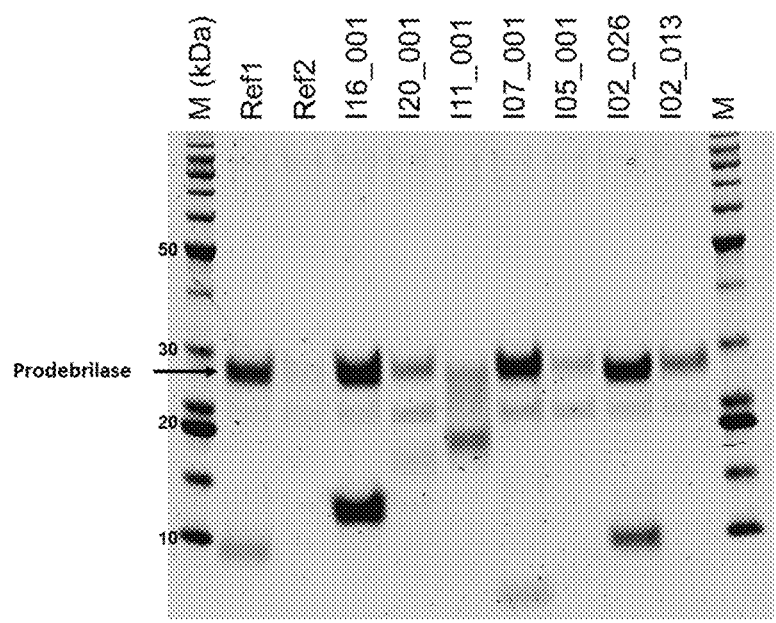

The MEROPS database for protease inhibitors was screened for aprotinin alternatives from different inhibitor groups. In order to test further inhibitors, 10 genes were selected: I02.013 tissue factor pathway inhibitor-2 inhibitor unit 1 (TFPI2), I02.018 chymotrypsin inhibitor SCI-1 (Chymotrypsin inhibitor SCI-1 (Clb1), I02.026 peptidase inhibitor 5 (KappaPI-actitoxin-Avd3a), I02.968 collagen alpha 3(VI) chain (CO6A3), I05.001 ascidian trypsin inhibitor, I07.001 trypsin inhibitor MCTI-1, I11.001 ecotin, I16.001 Plasminostreptin, I20.001 Proteinase inhibitor type-2 K (PIN2K), and I83.001 AmFPI-1. The genes were ordered as *P. pastoris* codon optimized DNA strings (Thermo Fisher Scientific). The plasmid pPpT4_P$_{AOX}$_Apr_Pp was cut with AatII and NotI for aprotinin removal. Gene strings were integrated into the opened pPpT4_P$_{AOX}$_Apr_Pp by homologous regions to the plasmid via Gibson cloning from New England Biolabs. Cloning was performed in *E. coli*. The sequence correctness of the constructed pPpT4 plasmids was verified by DNA sequencing and finally integrated into the genome of the original *P. pastoris* (U.S. Pat. No. 8,623,810 B2) expression strain as described in Example 2. For the expression of the new inhibitors in combination with debrilase, different *P. pastoris* transformants were cultivated for 52 hours in 96 well plates filled with 500 μl medium (m2p-labs Media Development Kit M-KIT-500). 25 μl of YPD (100 μg/mL Zeocin and 50 μg/mL Geneticin) precultures were inoculated in 500 μl expression medium per well. Glucose feed was induced by adding 1% v/v enzyme mix twice a day (0, 8, 24, 32 and 48 hours after inoculation). 0.5% v/v sterile methanol was added once 24 hours after inoculation and afterwards together with the enzyme mix to induce the aox1 promotor. After 52 hours, optical densities at 600 nm were determined and supernatants were harvested. Aurase activities were measured by using Z-Gly-Gly-Arg-AMC (Bachem) as substrate in a direct fluorometric assay. Clones that revealed no debrilase activity (7 inhibitor/debrilase combinations) compared to the original *P. pastoris* (U.S. Pat. No. 8,623,810 B2) expression strain were analyzed on SDS-PAGE for the analysis of inhibitor and debrilase production (FIG. 7). Debrilase was produced in satisfactory yields with all 10 tested inhibitors. An advantageous effect on the debrilase production was demonstrated for I16.001, I20.001, I11.001, I07.001, I05.001, I02.026, I02.013. The best effect on debrilase production was obtained with aprotinin and is demonstrated in the examples herein above. The molecular weight of the produced debrilase in combination with different inhibitors compared to the references *P. pastoris* (U.S. Pat. No. 8,623,810 B2) and *P. pastoris* AurPlus illustrates that debrilase is produced as prodebrilase like it was shown in example 3 in combination with aprotinin.

---

The invention claimed is:

1. A method for the recombinant production of debrilase comprising
    (a) culturing a host cell comprising one or more vectors, wherein the one or more vectors encode in expressible form debrilase and a proteinaceous inhibitor of debrilase under conditions wherein debrilase and the proteinaceous inhibitor of debrilase are expressed; or
    (a') culturing a host cell the genome of which encodes in expressible form debrilase and a proteinaceous inhibitor of debrilase wherein the coding sequences of debrilase and/or the proteinaceous inhibitor have been introduced into the host cell genome under conditions wherein debrilase and the proteinaceous inhibitor of debrilase are expressed; and
    (b) isolating debrilase expressed in step (a) or (a'),
    wherein the proteinaceous inhibitor of debrilase is selected from the group consisting of aprotinin, plasminostreptin (I16.001), proteinase inhibitor type-2 K (PIN2K, I20.001), ecotin (I11.001), trypsin inhibitor MCTI-1 (I07.001), ascidian trypsin inhibitor (I05.001), peptidase inhibitor 5 (KappaPI-actitoxin-Avd3a, I02.026), and tissue factor pathway inhibitor-2 inhibitor unit 1 (TFPI2, I02.013).

2. The method of claim 1, wherein debrilase is isolated in step (b) by size-exclusion chromatography, ion-exchange chromatography, affinity chromatography, or hydrophobic interaction chromatography.

3. The method of claim 1 further comprising (c) proteolytically processing the isolated debrilase.

4. A host cell
    (i) comprising one or more vectors, wherein the one or more vectors encode in expressible form debrilase and a proteinaceous inhibitor of debrilase, or
    (ii) the genome of which encodes in expressible form debrilase and a proteinaceous inhibitor of debrilase, wherein the coding sequences of debrilase and/or the proteinaceous inhibitor have been introduced into the host cell genome,
    wherein the proteinaceous inhibitor of debrilase is selected from the group consisting of aprotinin, plasminostreptin (I16.001), proteinase inhibitor type-2 K (PIN2K, I20.001), ecotin (I11.001), trypsin inhibitor MCTI-1 (I07.001), ascidian trypsin inhibitor (I05.001), peptidase inhibitor 5 (KappaPI-actitoxin-Avd3a, I02.026), and tissue factor pathway inhibitor-2 inhibitor unit 1 (TFPI2, I02.013).

5. The method of claim 1, wherein the host cell is
(a) a yeast cell;
(b) a bacterial cell; or
(c) a filamentous fungal cell.

6. The method of claim 1, wherein in the one or more vectors, debrilase is expressed from a first expression cassette and the proteinaceous inhibitor of debrilase is expressed from a second expression cassette.

7. The method of claim 6, wherein debrilase and the proteinaceous inhibitor of debrilase are under the control of the same or different regulated promoter(s).

8. The method of claim 7, wherein debrilase is under the control of the same regulated promoter as the proteinaceous inhibitor of debrilase.

9. The method of claim 8, wherein the host cell is a *Pichia pastoris* cell.

10. The method of claim 3, wherein proteolytically processing comprises the release of a propeptide from debrilase by proteolytic cleavage.

11. The method of claim 1, wherein the proteinaceous inhibitor of debrilase is aprotinin.

12. The host cell of claim 4, wherein the proteinaceous inhibitor of debrilase is aprotinin.

13. The method of claim 5, wherein:
(a) the yeast cell is a *Pichia pastoris* cell;
(b) the bacterial cell is a *Escherichia coli* or a *Bacillus subtilis* cell; and
(c) the filamentous fungal cell is an *Aspergillus* cell.

14. The method of claim 6, wherein the first and second expression cassettes are on two separate vectors.

15. The host cell of claim 4, wherein in the one or more vectors, debrilase is expressed from a first expression cassette and the proteinaceous inhibitor of debrilase is expressed from a second expression cassette.

16. The host cell of claim 15, wherein debrilase is under the control of the same regulated promoter as the proteinaceous inhibitor of debrilase.

17. The host cell of claim 15, wherein the first and second expression cassettes are on two separate vectors.

18. The method of claim 9, wherein the regulated promoter is $P_{aox}$ (alcohol oxidase promoter).

19. The method of claim 18, wherein the regulated promoter is $P_{aox1}$ or $P_{aox2}$.

* * * * *